United States Patent
Oota et al.

(10) Patent No.: US 8,279,450 B2
(45) Date of Patent: Oct. 2, 2012

(54) INTRA-ORAL MEASUREMENT DEVICE AND INTRA-ORAL MEASUREMENT SYSTEM

(75) Inventors: Sadafumi Oota, Osaka (JP); Seiji Hamano, Hyogo (JP); Fumio Sugata, Kanagawa (JP)

(73) Assignee: Panasonic Corporation, Osaka (JP)

( * ) Notice: Subject to any disclaimer, the term of this patent is extended or adjusted under 35 U.S.C. 154(b) by 354 days.

(21) Appl. No.: 12/693,558

(22) Filed: Jan. 26, 2010

(65) Prior Publication Data

US 2010/0189341 A1 Jul. 29, 2010

(30) Foreign Application Priority Data

Jan. 28, 2009 (JP) ................................. 2009-016321

(51) Int. Cl.
*G01B 11/24* (2006.01)
*G06K 9/00* (2006.01)
*A61B 1/24* (2006.01)

(52) U.S. Cl. ........ 356/601; 356/602; 356/603; 356/609; 382/154; 433/29

(58) Field of Classification Search .......... 356/600–625; 359/666, 820, 894, 823, 425; 433/29
See application file for complete search history.

(56) References Cited

U.S. PATENT DOCUMENTS

| | | | | |
|---|---|---|---|---|
| 4,575,805 A * | 3/1986 | Moermann et al. | ........... | 700/163 |
| 5,440,393 A * | 8/1995 | Wenz | ............................ | 356/611 |
| 5,528,432 A * | 6/1996 | Donahoo | ........................ | 359/894 |
| 5,671,056 A * | 9/1997 | Sato | ................................ | 356/602 |
| 5,917,657 A * | 6/1999 | Kaneko et al. | ................. | 359/661 |
| 6,263,234 B1 * | 7/2001 | Engelhardt et al. | ........... | 600/476 |
| 6,344,930 B1 * | 2/2002 | Kaneko et al. | ................. | 359/666 |
| 6,594,539 B1 * | 7/2003 | Geng | .............................. | 700/117 |
| 6,697,164 B1 * | 2/2004 | Babayoff et al. | .............. | 356/609 |
| 6,977,732 B2 * | 12/2005 | Chen et al. | ...................... | 356/603 |
| 7,142,312 B2 * | 11/2006 | Quadling et al. | .............. | 356/602 |
| 7,319,529 B2 * | 1/2008 | Babayoff | ........................ | 356/601 |
| 7,609,875 B2 * | 10/2009 | Liu et al. | ........................ | 382/154 |
| 2004/0152037 A1 | 8/2004 | Schick | | |
| 2004/0156626 A1 | 8/2004 | Thoms | | |
| 2005/0100333 A1 | 5/2005 | Kerschbaumer et al. | | |

(Continued)

FOREIGN PATENT DOCUMENTS

DE 101 25 772 12/2002

(Continued)

OTHER PUBLICATIONS

European Patent Office Search Report issued May 12, 2010 in counterpart European Application No. 10 15 1860.

*Primary Examiner* — Sang Nguyen
(74) *Attorney, Agent, or Firm* — Wenderoth, Lind & Ponack, L.L.P.

(57) ABSTRACT

The present invention aims to provide an intra-oral measurement device and an intra-oral measurement system capable of measuring an inside of an oral cavity at high accuracy without increasing a size of the device, and includes a light projecting unit for irradiating a measuring object including at least a tooth within an oral cavity with light, a lens system unit for collecting light reflected by the measuring object, a focal position varying mechanism for changing a focal position of the light collected by the lens system unit, and an imaging unit for imaging light passed through the lens system unit.

19 Claims, 17 Drawing Sheets

U.S. PATENT DOCUMENTS

2005/0168742 A1  8/2005  Jung et al.

FOREIGN PATENT DOCUMENTS

| EP | 1 529 485 | 5/2005 |
| EP | 1 780 575 | 5/2007 |
| EP | 1 941 843 | 7/2008 |
| JP | 2000-074635 | 3/2000 |
| WO | 2007/067776 | 6/2007 |

* cited by examiner

INTRA-ORAL MEASUREMENT DEVICE AND INTRA-ORAL MEASUREMENT SYSTEM

RELATED ART

The present invention relates to an intra-oral measurement device and an intra-oral measurement system capable of directly measuring an inside of an oral cavity.

A method of casting and fabricating metal material and ceramic material through a lost-wax casting process is generally adopted for a method of fabricating a dental prosthesis such as inlay, crown, and bridge.

However, a system of designing and fabricating a dental prosthesis using a CAD/CAM system after measuring an inside of an oral cavity for teeth and gingivae using an optical three-dimensional camera is recently given attention for a method of fabricating a dental prosthesis that takes a place of the lost-wax casting process. A typical example of such system is a CEREC system.

According to such system, a shape of an anchor tooth, a tooth having a cavity, adjacent dentition, dental antagonist, and the like is scanned directly in the oral cavity using an optical three-dimensional camera, thereby carrying out an intra-oral measurement of the teeth and gingivae. A camera for performing a non-contact three-dimensional measurement represented by a phase shift method and a space encoding method is used for the optical three-dimensional camera. As this type of the optical three-dimensional camera, for example, a camera described in Patent Document 1 (Japanese Unexamined Patent Publication No. 2000-74635) is known.

FIG. 21 is an explanatory view showing a configuration of a conventional optical three-dimensional camera.

Referring to FIG. 21, the conventional optical three-dimensional camera is provided with, within an external casing 101, a light source 102, a pattern mask 103, apertures 104, 105, a prism 106, and an imaging sensor 107 such as a CCD.

Light emitted from the light source 102 passes through the pattern mask 103 to form light in stripe pattern. The light in stripe pattern passes the aperture 104 so that an optical axis thereof is fine tuned, and then refracted by the prism 106 so as to be projected onto a measuring object 108. The light in stripe pattern projected onto the measuring object 108 is reflected by a surface of the measuring object 108 to thereby enter the prism 106, and then refracted by the prism 106. The refracted light passes through the aperture 105, and is received by the imaging sensor 107.

Data of a two-dimensional image received (imaged) by the imaging sensor 107 is transformed to data of three-dimensional coordinates through a triangulation method, so that the three-dimensional data of the measuring object 108 for designing and manufacturing the dental prosthesis is obtained by the CAD/CAM system.

The dental prosthesis can be efficiently fabricated, and the dental prosthesis having excellent adaptive accuracy to the inside of the oral cavity, compared to the lost-wax casting process, can be fabricated by using the conventional optical three-dimensional camera and the CAD/CAM system.

SUMMARY OF THE INVENTION

However, the conventional optical three-dimensional camera uses the triangulation method. Thus, an expected angle between an optical axis on a light projecting side and an optical axis on an imaging side needs to be made large to enhance measurement accuracy. A size of the optical three-dimensional camera needs to be increased in order to have a large expected angle, but increasing the size has limits as the optical three-dimensional camera is to be inserted into an oral cavity. Therefore, enhancing the measurement accuracy in the conventional optical three-dimensional camera is difficult.

It is therefore an object of the present invention to solve the above problems, and to provide an intra-oral measurement device and an intra-oral measurement system enabling an inside of the oral cavity to be measured at high accuracy without increasing the size of the device.

In order to achieve the above object, the present invention is configured as described below.

According to a first aspect of the present invention, there is provided an intra-oral measurement device including: a light projecting unit for irradiating a measuring object including at least a tooth within an oral cavity with light; a lens system unit for collecting light reflected by the measuring object; a focal position varying mechanism for changing a focal position of the light collected by the lens system unit; and an imaging unit for imaging light passed through the lens system unit.

According to a second aspect of the present invention, there is provided the intra-oral measurement device according to the first aspect, wherein a liquid lens is used for the focal position varying mechanism.

According to a third aspect of the present invention, there is provided the intra-oral measurement device according to the first or second aspect, further including a pre-scan light projecting device for emitting guide light focused at a position distant from the light projecting unit by a distance set in advance.

According to a fourth aspect of the present invention, there is provided the intra-oral measurement device according to the third aspect, wherein the pre-scan light projecting device emits linear light passing through the position distant from the light projecting unit by the distance set in advance.

According to a fifth aspect of the present invention, there is provided the intra-oral measurement device according to the third or fourth aspect, further including an image processing unit, which does not image the light passed through the lens system unit with the imaging unit when a circularity of the guide light emitted from the pre-scan light projecting device and projected onto the measuring object is lower than a threshold value set in advance, and images the light passed through the lens system unit with the imaging unit when the circularity of the guide light is higher than the threshold value set in advance.

According to a sixth aspect of the present invention, there is provided the intra-oral measurement device according to any one of the third to fifth aspects, further including an image processing unit, which does not image the light passed through the lens system unit with the imaging unit when an amount of shift between a light quantity distribution of the guide light emitted from the pre-scan light projecting device and projected onto the measuring object and an ideal light quantity distribution of the guide light is lower than a threshold value set in advance, and images the light passed through the lens system unit with the imaging unit when the amount of shift is higher than the threshold value set in advance.

According to a seventh aspect of the present invention, there is provided the intra-oral measurement device according to any one of the first to sixth aspects, further including an image processing unit for calculating three-dimensional coordinates of the measuring object using a plurality of images, having different focal positions, imaged by the imaging unit.

According to an eighth aspect of the present invention, there is provided the intra-oral measurement device according to the seventh aspect, wherein the image processing unit calculates the three-dimensional coordinates of the measuring object using the images having different focal positions associated with a response speed of the focal position varying mechanism.

According to a ninth aspect of the present invention, there is provided the intra-oral measurement device according to any one of the first to eighth aspects, wherein the light projecting unit irradiates an inside of the oral cavity with light having a plurality of different wavelengths.

According to a tenth aspect of the present invention, there is provided the intra-oral measurement device according to the ninth aspect, wherein the light having different wavelengths include light having a wavelength of between 500 and 565 nm, and light having a wavelength of between 625 and 740 nm.

According to an eleventh aspect of the present invention, there is provided the intra-oral measurement device according to any one of the first to tenth aspects, further including a gap retaining member for holding a gap between the tooth and the light projecting unit constant.

According to a twelfth aspect of the present invention, there is provided the intra-oral measurement device according to the eleventh aspect, wherein the gap retaining member has a two-layered structure in which a distal end portion, which is a side that comes in contact with the tooth, is soft and a main body portion, which is a side fixed to the device, is harder than the distal end portion.

According to a thirteenth aspect of the present invention, there is provided an intra-oral measurement system including: a light projecting unit for irradiating a measuring object including at least a tooth within an oral cavity with light; a lens system unit for collecting light reflected by the measuring object; a focal position varying mechanism for changing a focal position of the light collected by the lens system unit; an imaging unit for imaging light passed through the lens system unit; and an image processing unit for calculating three-dimensional coordinates of the measuring object using a plurality of images, having different focal positions, imaged by the imaging unit.

BRIEF DESCRIPTION OF THE DRAWINGS

These and other aspects and features of the present invention will become clear from the following description taken in conjunction with the embodiments thereof with reference to the accompanying drawings, in which.

DETAILED DESCRIPTION OF THE INVENTION

Embodiments of the present invention will now be described with reference to the drawings. In the following description, the same reference numbers are given to the same configurations and the description thereof will not be given.

First Embodiment

Figure 1:
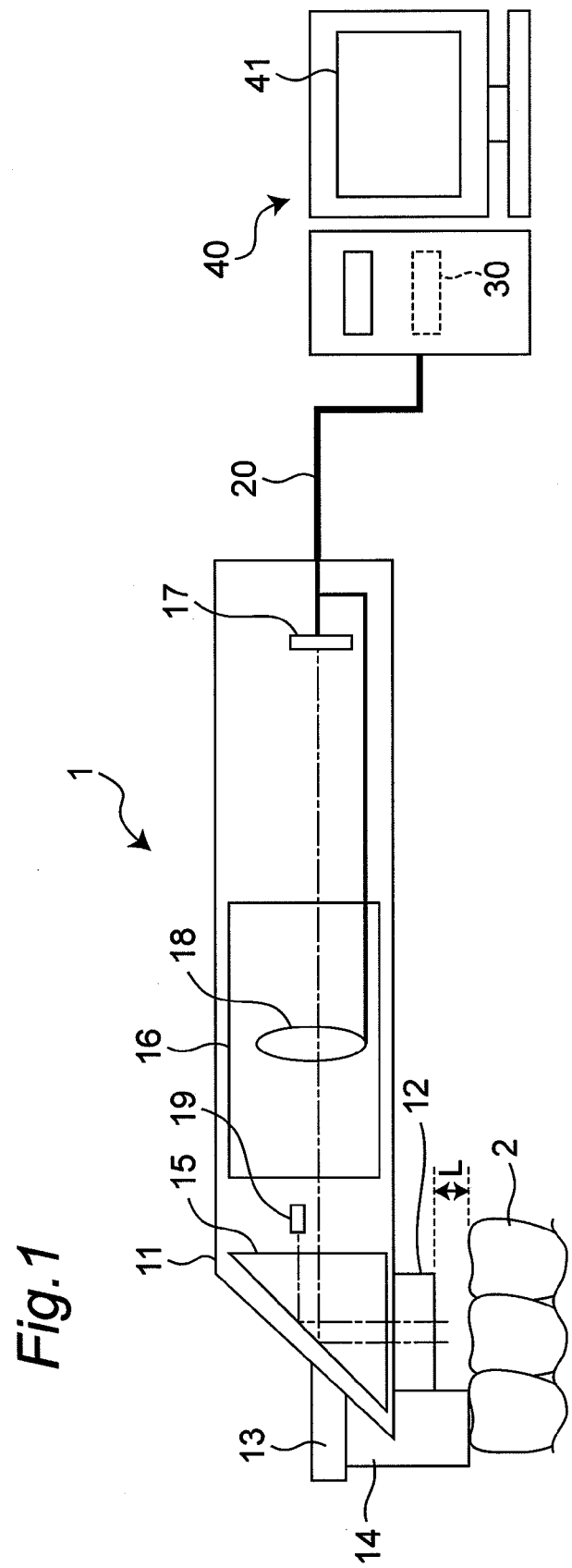
FIG. 1 is an explanatory view showing a schematic configuration of an intra-oral measurement system including an oral scanner according to a first embodiment of the present invention.
Figure 2:
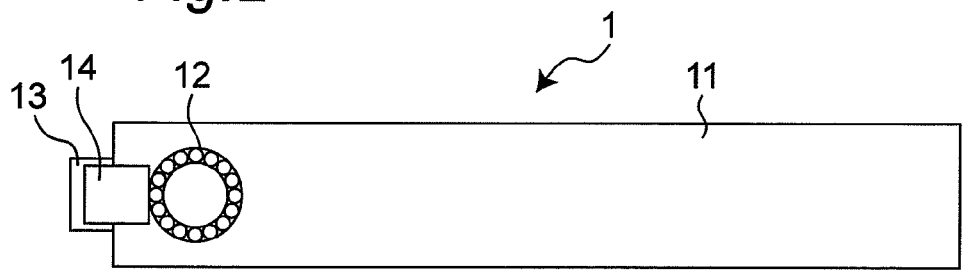
FIG. 2 is a view of the oral scanner shown in FIG. 1 seen from downside.

FIG. 1 is an explanatory view showing a schematic configuration of an intra-oral measurement system including an intra-oral measurement device (hereinafter referred to as oral scanner) according to a first embodiment of the present invention. FIG. 2 is a schematic view of the oral scanner shown in FIG. 1 seen from side.

As shown in FIG. 1, the oral scanner 1 includes an outer case 11 of a size capable of being directly inserted into an oral cavity of a patient. An outer dimension of the oral scanner 1 is, for example, a length of 200 mm, a width of 20 mm, and a height of 25 mm. A light projecting unit 12 is attached at a distal end portion of the outer case 11 as a light source for clearly taking an image of a measuring object 2 including at least a tooth. A light emitting diode (LED), laser, a halogen lamp, or the like is used for the light projecting unit 12. As shown in FIG. 2, the light projecting unit 12 has a structure in which a plurality of light emitting diodes are annularly arranged. In this case, the light projecting unit 12 is assumed to emit light having a wavelength region of between 500 and 565 nm in which a surface reflectivity of enamel of the tooth is high.

A rubber attachment portion 13 is also arranged at the distal end portion of the outer case 11, and a rubber 14 serving as a gap retaining member is removably attached to the rubber attachment portion 13. As shown in FIG. 2, the rubber 14 is arranged adjacent to the light projecting unit 12. The rubber 14 is a disposable member for holding a gap between the light projecting unit 12 and the measuring object 2 to a constant distance L (e.g., 5 mm), and is made of a material that does not present any hygienic problems. The rubber 14 has a predetermined hardness so as to hold the gap between the light projecting unit 12 and the measuring object 2 constant, but the distal end portion thereof is formed soft so as to deform according to a shape of a portion where the distal end comes in contact within the oral cavity. For example, the rubber 14 is configured by a rubber having a two-layered structure in which the material differs at a main body portion and a distal end portion. In the present embodiment, the rubber in which a hardness of the main body portion of the rubber 14 is smaller than or equal to a rubber hardness of 90 and a hardness of the distal end portion of the rubber 14 is smaller than or equal to a rubber hardness of 70 is used. The rubber hardness is a shore hardness by Durometer A complying with JIS K 6253-1997 (ISO 7619).

Figure 3:
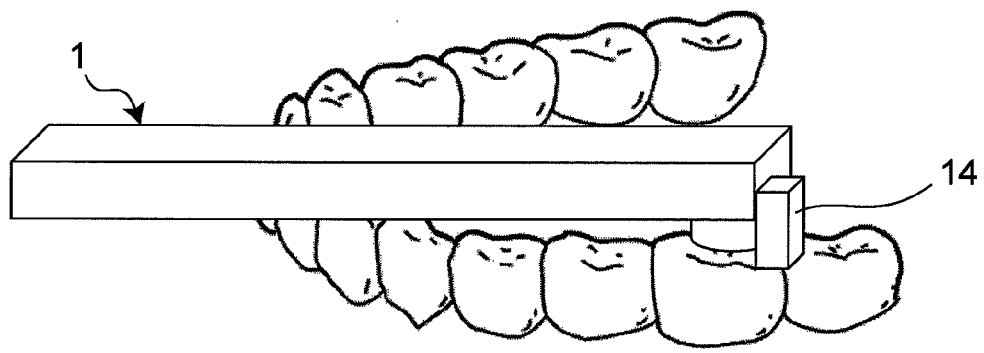
FIG. 3 is a schematic perspective view showing a state of measuring a surface shape of a back tooth of a patient using the oral scanner shown in FIG. 1.

When measuring a surface shape of a back tooth of the patient using the oral scanner 1, the position of the oral scanner 1 is adjusted so that the rubber 14 comes in contact with a portion adjacent to the measuring object 2 (e.g., tooth adjacent to the tooth to be measured), as shown in FIG. 3.

Figure 4:
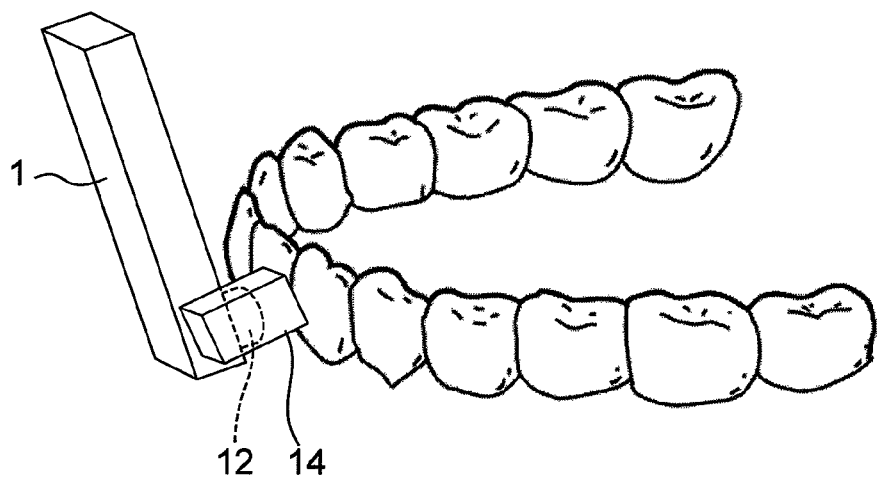
FIG. 4 is a schematic perspective view showing a state of measuring a surface shape of a front tooth of a patient using the oral scanner shown in FIG. 1.

An attachment position and the number of rubbers 14 are not particularly limited, and may be appropriately set according to the measuring object 2. For example, when measuring a surface shape of a front tooth of a patient using the oral scanner 1, the rubber is suitably attached on a side surface instead of the distal end side of the oral scanner 1, as shown in FIG. 4. In FIGS. 3 and 4, a configuration of the oral scanner 1 is shown in a simplified manner.

A prism 15, a lens system unit 16, and an imaging sensor 17 such as a CCD (Charge Coupled Device) serving as an imaging unit are arranged in series inside the outer case 11.

The prism 15 refracts the light emitted from the light projecting unit 12 to the measuring object 2 and reflected by the measuring object 2 towards the lens system unit 16. The lens system unit 16 focuses the light refracted by the prism 15 to the imaging sensor 17 for image forming. The lens system unit 16 is a telecentric lens system configured such that a size of an image taken at an imaging plane does not change depending on a focal position. The lens system unit 16 includes a cylindrical liquid lens 18. The liquid lens 18 serves as a focal position varying mechanism capable of changing the focal position according to an applied voltage. A configuration of the liquid lens 18 will be described in detail below.

A spot light source 19 serving as a pre-scan light projecting device is attached between the prism 15 and the lens system unit 16. The spot light source 19 is configured to emit guide light towards the prism 15 to focus (converge) at a position distant from the distal end of the light projecting unit 12 by a distance (e.g., 10 mm) set in advance.

Figure 5:
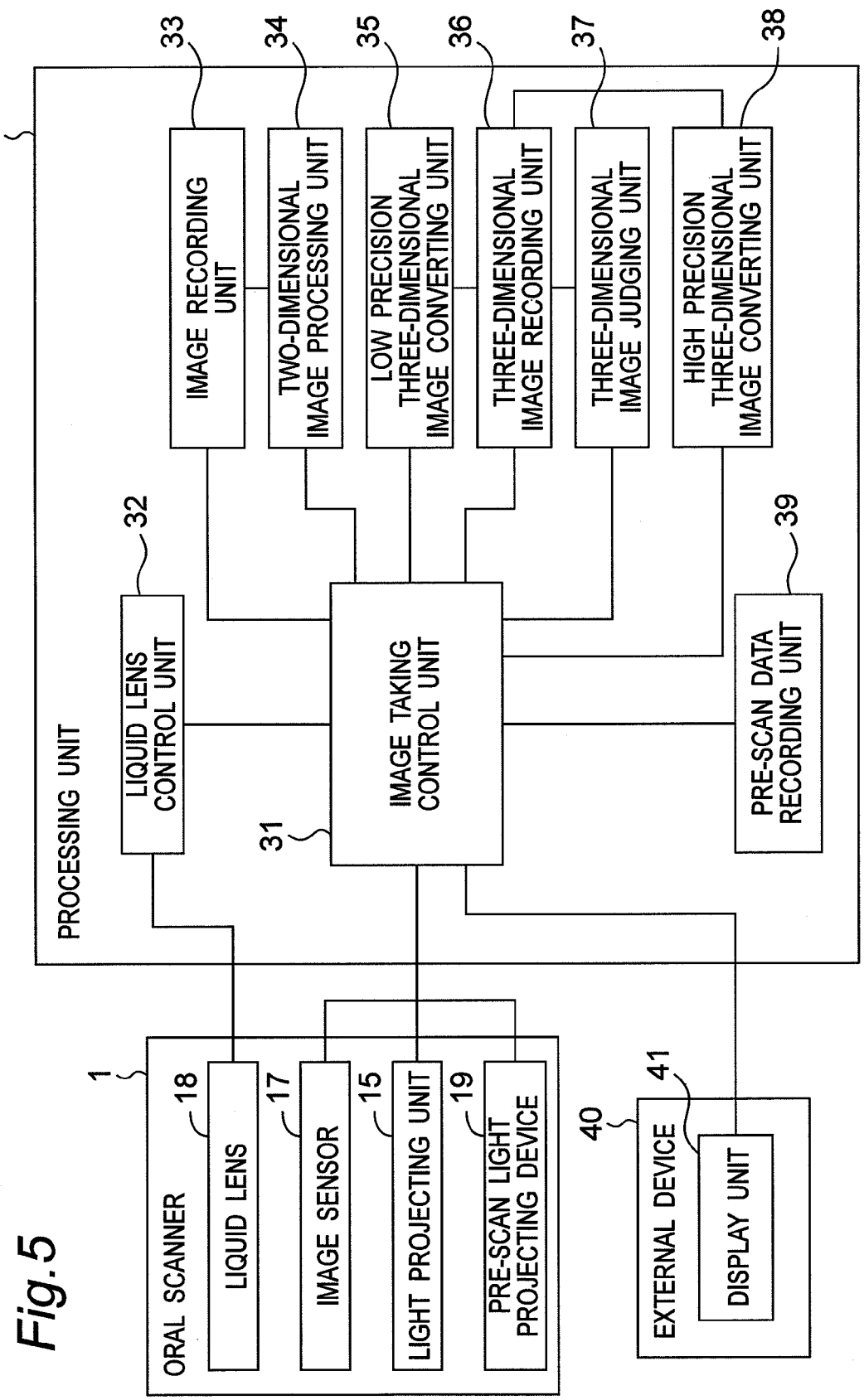
FIG. 5 is a block diagram of the intra-oral measurement system shown in FIG. 1.

The imaging sensor 17 picks up (receives) the light passed through the lens system unit 16. Data of a two-dimensional image received by the imaging sensor 17 is transferred to an image processing unit 30 through a transfer cable 20. The image processing unit 30 is housed in an external device 40 such as a personal computer. The image processing unit 30 transforms the transferred two-dimensional image data to three-dimensional coordinate data, and obtains three-dimensional data of the measuring object 2 for designing and manufacturing of a dental prosthesis. As shown in FIG. 5, the image processing unit 30 includes a image taking control unit 31, a liquid lens control unit 32, an image recording unit 33, a two-dimensional image processing unit 34, a low precision three-dimensional image converting unit 35, a three-dimensional image recording unit 36, a three-dimensional image judging unit 37, a high precision three-dimensional image converting unit 38, and a pre-scan data recording unit 39. Functions of each unit of the image processing unit 30 will be described in detail below.

Figure 6A:
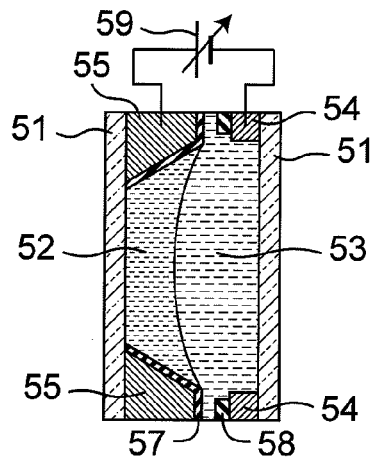
FIG. 6A is a schematic cross-sectional view of a liquid lens mounted on the oral scanner shown in FIG. 1.
Figure 6B:
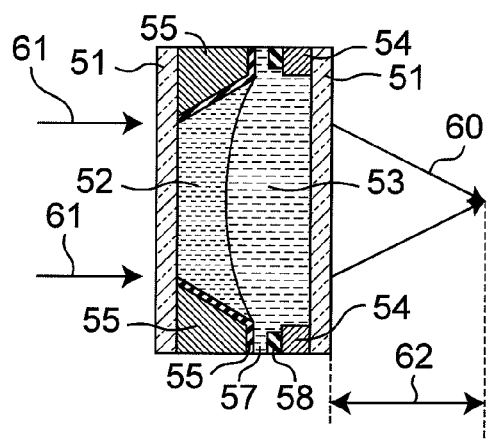
FIG. 6B is a cross-sectional view showing a relationship between the liquid lens and a focal position when a voltage is not applied.
Figure 6C:
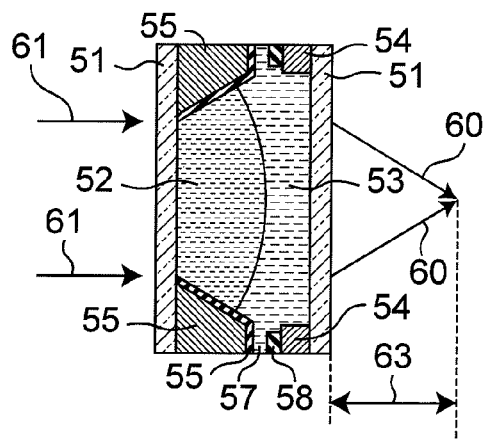
FIG. 6C is a cross-sectional view showing a relationship between the liquid lens and the focal position when a voltage is applied.

The configuration and a function of the liquid lens 18 will now be described in detail with reference to FIGS. 6A to 6C. FIG. 6A is a cross-sectional view showing the configuration of the liquid lens. FIG. 6B is a cross-sectional view showing a relationship between the liquid lens and the focal position when a voltage is not applied. FIG. 6C is a cross-sectional view showing a relationship between the liquid lens and the focal position when a voltage is applied.

As shown in FIG. 6A, the liquid lens 18 includes two protective glasses 51, 51, an oil layer 52 and an aqueous solution layer 53 stacked between the two protective glasses 51, 51, electrode portions 54, 55, arranged at a periphery thereof, for applying a voltage, and insulating portions 57, 58 for insulating the electrode portions 54, 55. A variable voltage source 59 is connected to the electrode portions 54, 55.

The liquid lens 18 has characteristics in that a curvature radius and a thickness of the oil layer 52 change when the voltage applied to the electrode portions 54, 55 by the variable voltage source 59 changes, thereby changing a focal position of light 60 passed through the liquid lens 18. More specifically, when a predetermined voltage is applied to the electrode portions 54, 55 in the state of FIG. 6B, the curvature radius and the thickness of the oil layer 52 become large as shown in FIG. 6C. Thus, the focal length 63 shown in FIG. 6C becomes short with respect to the focal length 62 shown in FIG. 6B when parallel light rays 61, 61 enters the liquid lens 18, as shown in FIGS. 6B and 6C. In other words, the focal length can be reduced by increasing the voltage to apply to the electrode portions 54, 55.

In the first embodiment, the liquid lens 18 is used as a focal position varying mechanism because an outer shape of a typical liquid lens is small, or smaller than or equal to 10 mm, even including the electrode portion, and a response speed from when the voltage is applied until the change of the focal position is completed is fast, which is about 20 msec.

Figure 7:
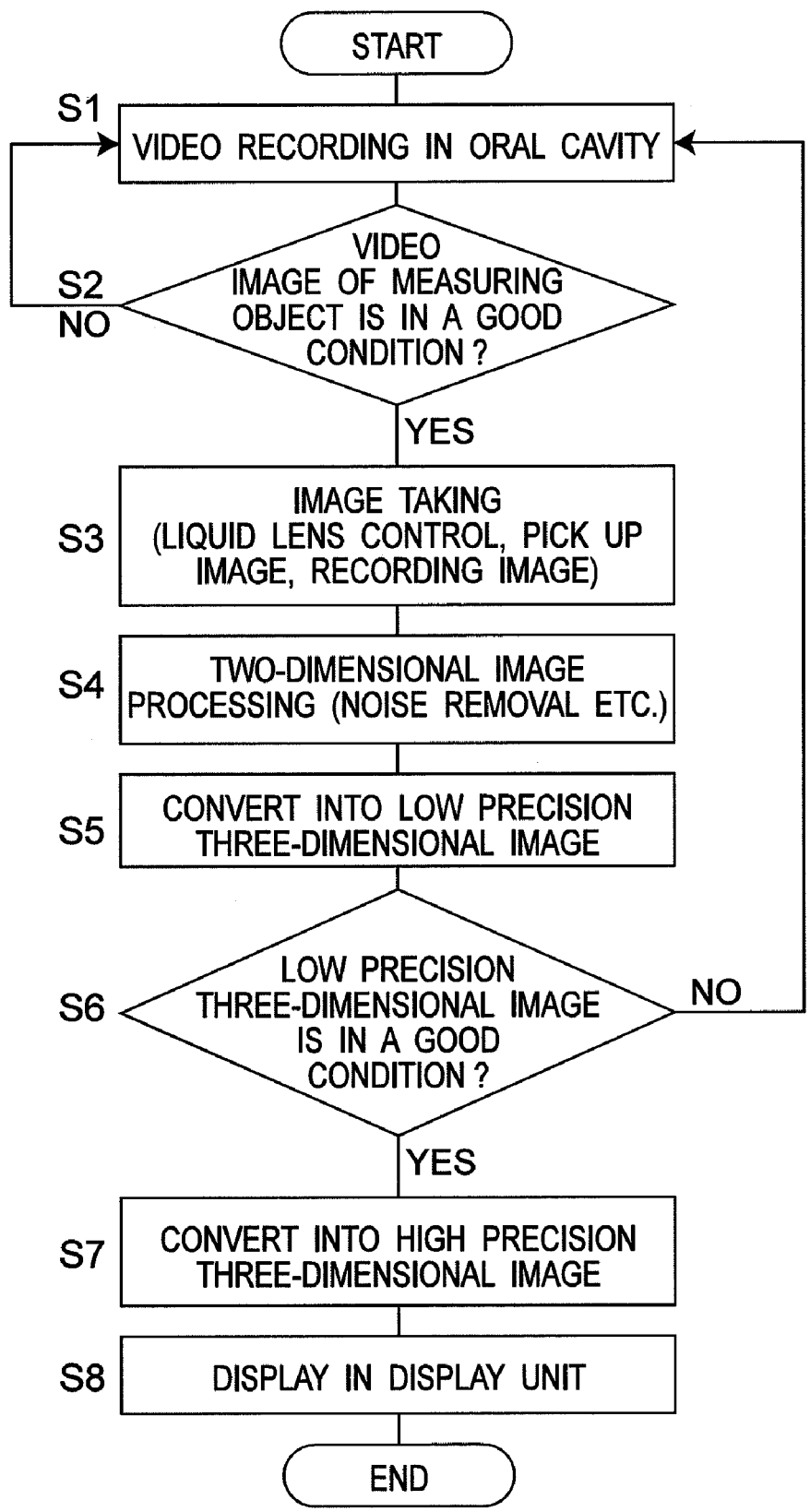
FIG. 7 is a flowchart for measuring an inside of an oral cavity using the intra-oral measurement system according to the first embodiment of the present invention.

The intra-oral measurement method by the intra-oral measurement system according to the first embodiment will now be described with reference to FIGS. 1, 5, and 7. FIG. 7 shows a flowchart for measuring the inside of the oral cavity using the intra-oral measurement system according to the first embodiment.

First, the oral scanner 1 is set in the oral cavity of a patient (see e.g., FIGS. 3 and 4), and a dentist pushes a video recording start button (not shown) of the external device 40 to start video recording of the inside of the oral cavity by the oral scanner 1 (step S1). In this case, the distance L between the measuring object 2 and the light projecting unit 12 is held constant (e.g., 5 mm) by the rubber 14. The video recording by the oral scanner 1 is carried out, under the control of the image taking control unit 31, by irradiating the light from the light projecting unit 12, and receiving the light reflected on the measuring object 2 and received by the imaging sensor 17. The video image taken by the oral scanner 1 is transferred to the image taking control unit 31 through the transfer cable 20, and displayed in the display unit 41 of the external device 40 under the control of the image taking control unit 31. Here, the oral scanner 1 carries out an operation similar to a common video camera.

Then, the oral scanner 1 is moved so that the measuring object 2 is correctly displayed in the display unit 41, and it is confirmed whether or not a video image of the displayed measuring object 2 is in good condition (step S2). For example, if the LED light source having an output of 3 W is used for the light projecting unit 12 and a luminance value is expressed with 256 gray levels, the video image is judged as in a good condition if the average gray level of the measuring object 2 (e.g., gingivae) is greater than or equal to 40 gray level. It is noted that this judgment can be made by the dentist, or can be automatically made by the image processing unit 30. If the video image of the measuring object 2 is not in a good condition, various settings and measurement positions are adjusted so that the video image becomes in a good condition. If the video image of the measuring object 2 is in a good condition, the image of the measuring object 2 is picked up (step S3). It is preferable that the picking up is carried out by, for example, the dentist stepping on a foot operated switch provided for a treatment table.

After obtaining one image data (two-dimensional still image) of the measuring object 2, the voltage to apply to the liquid lens 18 is changed by the control of the liquid lens control unit 32 to change the focal position of the light passed through the liquid lens 18. Thereafter, the image of the measuring object 2 is picked up under the control of the image taking control unit 31. This operation is repeated to obtain a plurality of image data of the measuring object 2. As will be specifically described below, the continuous picking up of images of the measuring object 2 is automatically performed under the control of the image taking control unit 31. The obtained image data of the measuring object 2 is recorded in the image recording unit 33 in association with the focal position. The images obtained here, other than those which focal position matches the imaging plane of the imaging sensor 17, cause a so-called image blur.

Next, the plurality of obtained image data pieces of the measuring object 2 are synthesized in the following manner.

First, the two-dimensional image processing unit 34 performs two-dimensional image processing such as gray level correction, noise removal, conversion from analog signal to digital signal, and the like on the image data recorded in the image recording unit 33 (step S4).

Then, the low precision three-dimensional image converting unit 35 synthesizes 10% to 50% of the plurality of two-dimensional image processed image data after converting to three-dimensional coordinates. Thereby, a low precision three-dimensional image is obtained (step S5). The low precision three-dimensional image is recorded in the three-dimensional image recording unit 36. The method for the synthesizing process of the three-dimensional images will be described in detail below.

Then, the three-dimensional image judging unit 37 judges whether or not the low precision three-dimensional image is in a good condition (step S6).

Figure 8:
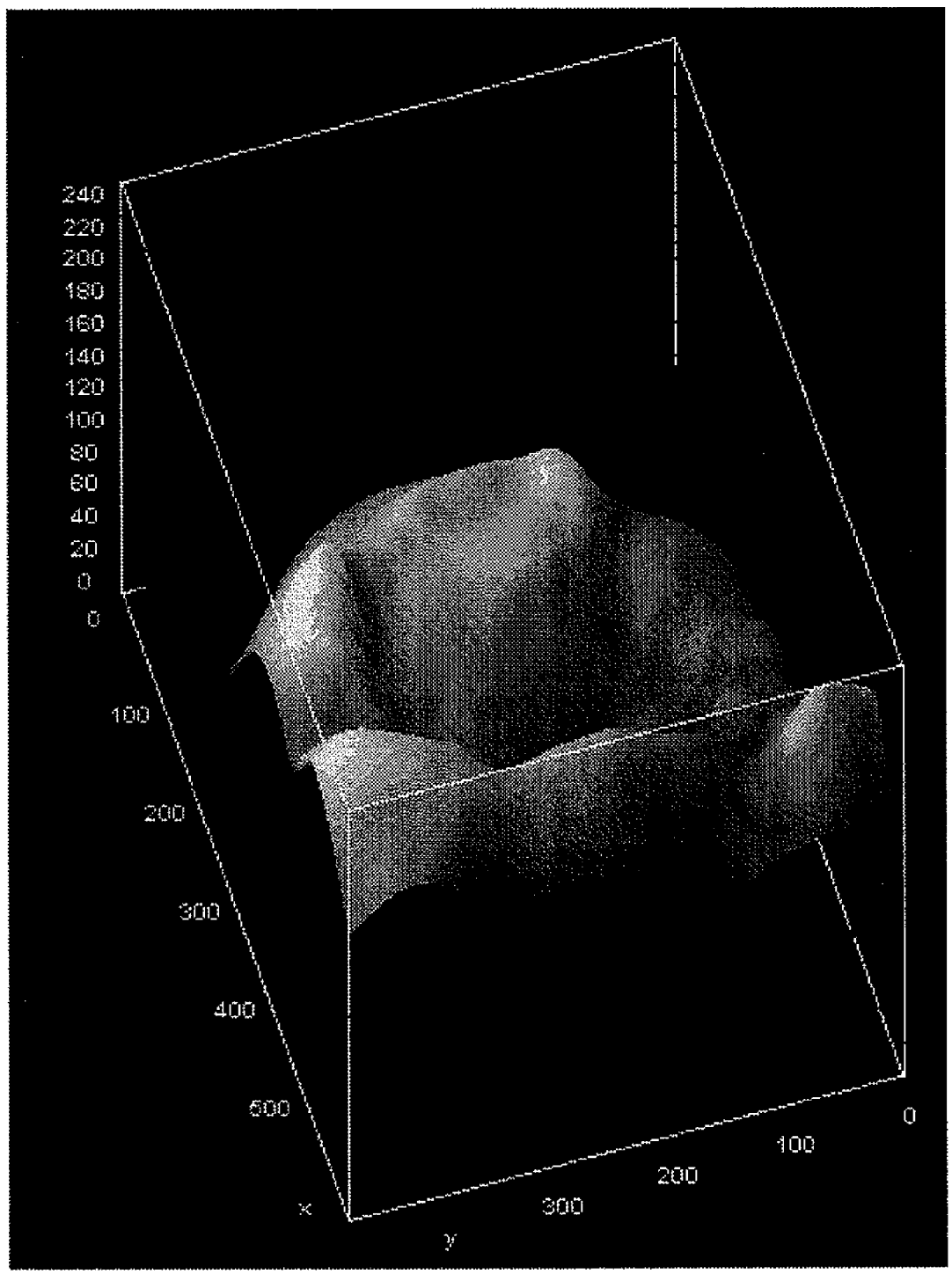
FIG. 8 is a view showing a three-dimensional image of a measuring object.

Thereafter, if the three-dimensional image judging unit 37 judges that the low precision three-dimensional image is not in a good condition, the process returns to step S1. On the other hand, if the three-dimensional image judging unit 37 judges that the low precision three-dimensional image is in a good condition, the high precision three-dimensional image converting unit 38 synthesizes all two-dimensional image processed image data after converting to the three-dimensional coordinates. In this manner, the high precision three-dimensional image as shown in FIG. 8 is obtained (step S7). The obtained high precision three-dimensional image is recorded in the three-dimensional image recording unit 36, and displayed in the display unit 41 (step S8).

The steps S6, S7 are performed as the obtained three-dimensional image may differ from a surface shape of the measuring object 2 due to faulty imaging and the like and time required until obtaining the three-dimensional image may become a waste. Therefore, the steps S6, S7 are not necessarily required steps.

Furthermore, the judgment of whether or not the low precision three-dimensional image is a good condition in step S7 as described above can be carried out by the dentist by displaying the low precision three-dimensional image in the display unit 41. Specifically, in this case, the dentist compares a shape of the measuring object 2 that the dentist sees with the shape of the measuring object 2 in the low precision three-dimensional image, and judges whether or not the low precision three-dimensional image in a good condition.

Figure 9:
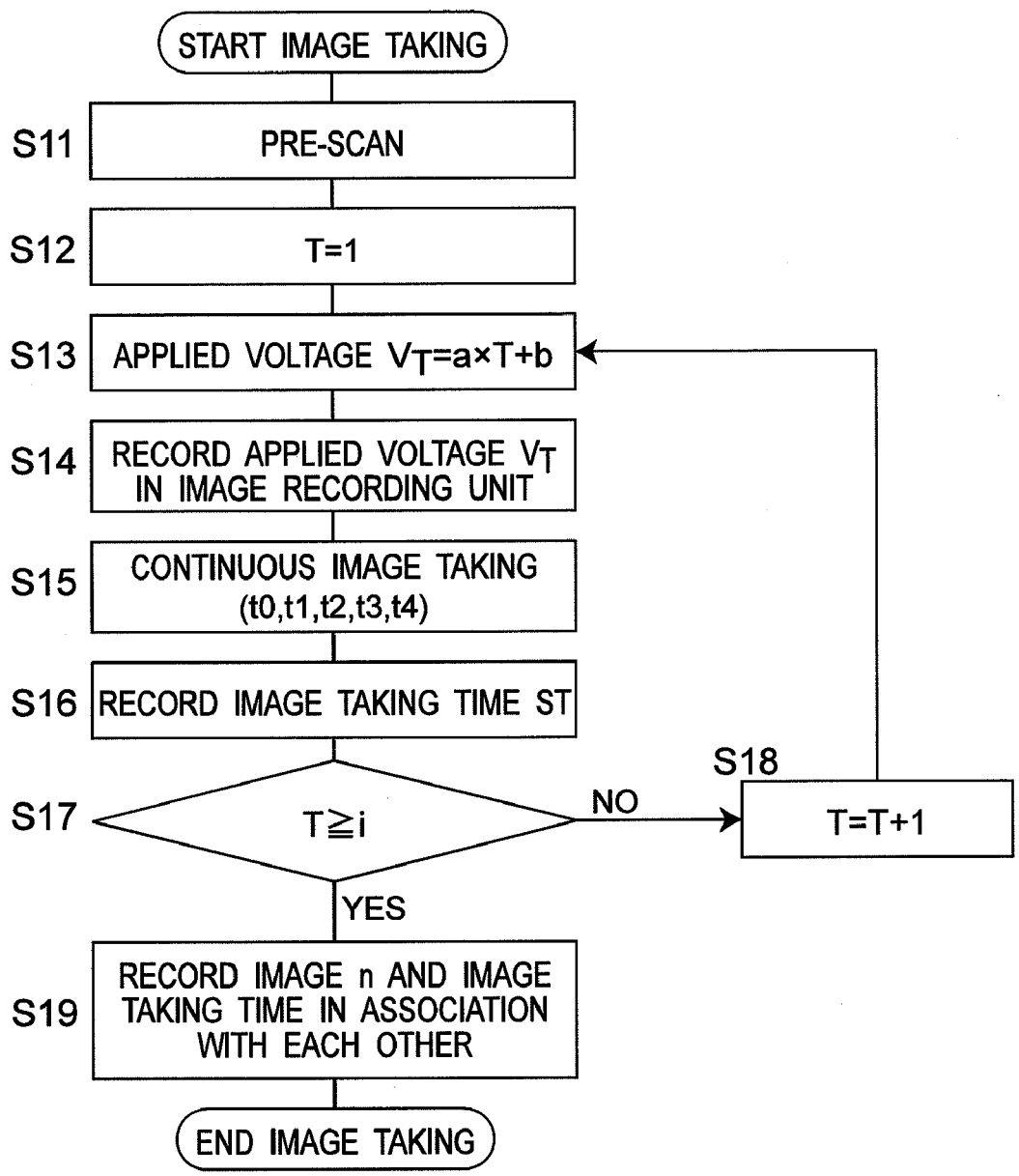
FIG. 9 is a flowchart of the image taking of the measuring object in the intra-oral measurement system according to the first embodiment of the present invention.

A flow of the image taking of the measuring object 2 will now be described with reference to FIGS. 1, 5, and 9. FIG. 9 is a flowchart of taking the image of the measuring object in the intra-oral measurement system according to the first embodiment. It is noted that the image taking of the measuring object 2 is carried out under the control of the image taking control unit 31, unless otherwise stated.

First, the oral scanner 1 is moved so that the measuring object 2 is correctly displayed in the display unit 41. If the video image of the measuring object 2 is in a good condition (step S2), the dentist sets a pre-scanning position (XY coordinate) while referencing the video image of the measuring object 2. The setting of the pre-scanning position is not particularly limited, but the dentist can set the pre-scanning position by pushing a desired position of the measuring object 2 displayed in the display unit 41 if the display unit 41 is a touch panel type. Guide light is emitted from the spot light source 19 towards the set pre-scanning position (XY coordinate), and a schematic position (XYZ coordinate) of the measuring object 2 is measured (step S11).

As described above, the guide light is emitted so as to be refracted by the prism 15, and focused (converged) at a predetermined depth (Z direction position) from the light projecting unit 12. In this case, the predetermined depth is 10 mm from the light projecting unit 12. The guide light emitted in the above manner is reflected at a guide light reflection point of the measuring object 2 and enters the prism 15, and then refracted by the prism 15, passed through the liquid lens 18, and received by the imaging sensor 17. The depth of the guide light reflection surface is obtained based on the image blur amount of the measuring object 2 received by the imaging sensor 17. This operation is called the pre-scan herein. The relationship between the image blur amount of the measuring object 2 and the predetermined depth is recorded in advance in the pre-scan data recording unit 39.

The image blur amount of the measuring object 2 is determined by a distance between the guide light reflection surface (pre-scan surface) of the measuring object 2 and the focus of the guide light. Thus, the image blur amount is the same for when the guide light reflection surface of the measuring object 2 is positioned at a depth of 9 mm from the light projecting unit 12 and for when the guide light reflection surface is positioned at a depth of 11 mm. Whether the guide light reflection surface of the measuring object 2 is judged at the depth of 9 mm or positioned at the depth of 11 mm can be determined by changing the focal position. By changing the focal position, a difference is generated in the image blur amount received by the imaging sensor 17 for when the guide light reflection surface is positioned at the depth of 9 mm and for when the guide light reflection surface is positioned at the depth of 11 mm. Therefore, the position (depth) of the guide light reflection surface of the measuring object 2 can be known by examining the difference in the image blur amount. If the position (depth) of the guide light reflection surface of the measuring object 2 is known, an outline of a size of a recess of the measuring object 2 to measure can be known. Accordingly, the range of the voltage to apply to the liquid lens 18 to change the focal position can be narrowed, and the image taking time can be shortened.

If the spot diameter (diameter of focus) of the guide light is large, the measurement accuracy of the pre-scan may be lowered by an influence of the shape of the pre-scan surface of the measuring object 2. For example, if the spot diameter of the guide light is 2.0 mm and the pre-scan surface is inclined 45 degrees with respect to the guide light, the measurement accuracy of the pre-scan lowers by about 2.0 mm. Since a positioning of the oral scanner 1 is performed by the dentist, it is difficult to hold the oral scanner 1 such that the pre-scan surface is always orthogonal to the irradiation direction of the guide light. Thus, the spot diameter of the guide light is preferably made as small as possible (e.g., smaller than or equal to 1.0 mm). Reducing the spot diameter of the guide light has physical limits. In this case, the following process is considered effective.

In other words, if the pre-scan surface is orthogonal to the irradiation direction of the guide light, a shape of the guide light projected on the measuring object 2 becomes a perfect circle. On the other hand, if the pre-scan surface is inclined with respect to the irradiation direction of the guide light, the shape of the guide light becomes an ellipse. In other words, low circularity of the guide light means large inclination angle of the pre-scan surface with respect to the irradiation direction of the guide light. Thus, the dentist preferably fine tunes the position of the oral scanner 1 and continues the pre-scan until the circularity of the guide light becomes higher than the preset threshold value. In other words, the measuring object 2 is not received by the imaging sensor 17 if the circularity of the guide light is lower than the preset threshold value, and the measuring object 2 is received by the imaging sensor 17 if the circularity of the guide light is higher than the preset threshold value. The measurement accuracy of the pre-scan can be enhanced by examining the depth based on the image blur amount of the measuring object 2 taken in the above manner. In the embodiment 1, the position of the oral scanner 1 can be easily fine tuned by the dentist since the rubber 14 is soft and can be deformed according to a shape of the portion where the rubber 14 come into contact within the oral cavity.

Furthermore, the pre-scan surface sometimes has irregularities (Z direction) within the range of the spot diameter of the guide light since the measuring object 2 is an object with a complex shape such as tooth. In this case, the light quantity distribution of the guide light reflected by the measuring object 2 differs from when the pre-scan surface does not have irregularities. Thus, the dentist preferably fine tunes the position of the oral scanner 1 and continues the pre-scan until the amount of shift between the light quantity distribution of the guide light reflected by the measuring object 2 and the ideal light quantity distribution of the guide light (e.g., light quantity distribution of the guide light when the pre-scan surface does not have irregularities at all) becomes lower than a preset threshold value. In other words, the measuring object 2 is not received by the imaging sensor 17 if the amount of shift is smaller than the preset threshold value, and the measuring object 2 is received by the imaging sensor 17 if the amount of shift is greater than the preset threshold value. The measurement accuracy of the pre-scan can be enhanced by examining the depth based on the image blur amount of the measuring object 2 taken in the above manner. The threshold value is preferably set such that a proportion of the amount of shift with respect to the ideal light quantity distribution of the guide light becomes smaller than or equal to 20%. This is because the process becomes more complicating if the proportion exceeds 20%.

After the pre-scan (step S11) is finished, a variable T=1 is set (step S12), and a voltage $V_T$ is applied to the liquid lens 18 by the control of the liquid lens control unit 32 (step S13). The voltage $V_T$ and the variable T are in a relationship of a linear function ($V_T$=aT+b (a, b are constants)). Therefore, the voltage $V_T$ changes proportional to the change of the variable T. Assume $V_T$=−2T+53. In other words, when the variable is T=1, the voltage $V_T$ to apply to the liquid lens 18 is 51V. The voltage $V_T$ applied to the liquid lens 18 is recorded in the image recording unit 33 (step S14).

After the voltage is applied to the liquid lens 18, the light passed through the liquid lens 18 is continuously received by the imaging sensor 17 at five times t0, t1, t2, t3, and t4 (step S15).

Figure 10A:
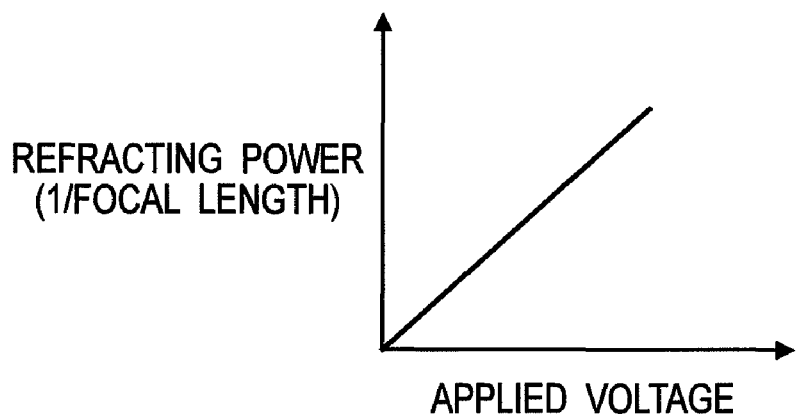
FIG. 10A is a graph showing a relationship between refracting power (inverse number of focal length) of the liquid lens and an applied voltage.
Figure 10B:
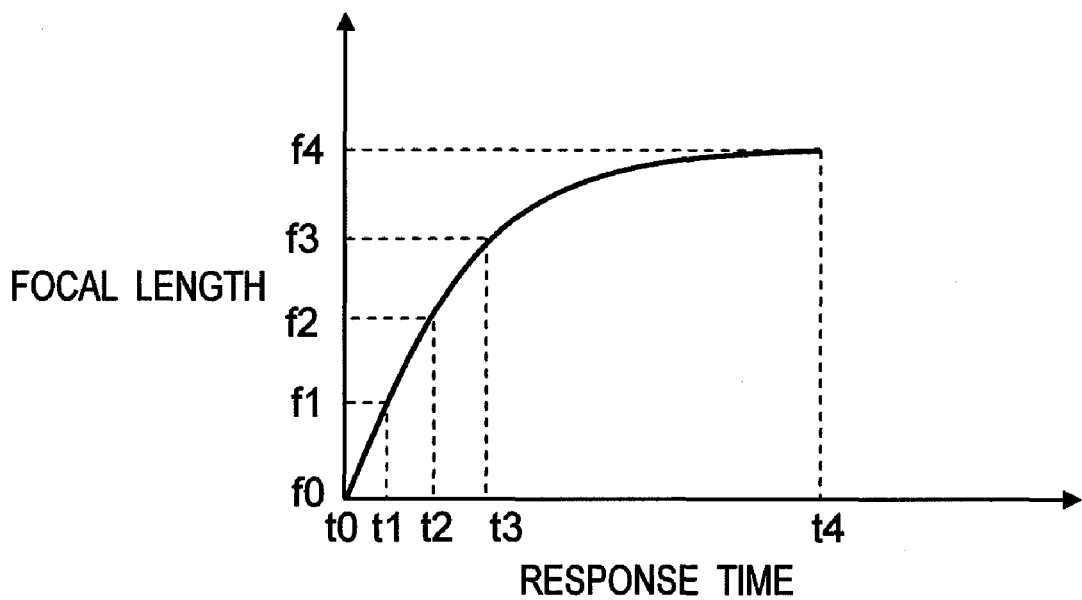
FIG. 10B is a graph showing a relationship between the focal length of the liquid lens and response time.

FIG. 10A is a graph showing a relationship between the refracting power (inverse number of focal length) of the liquid lens 18 and the applied voltage; and FIG. 10B is a graph showing a relationship between the focal length of the liquid lens 18 and the response time. As shown in FIG. 10A, the refracting power of the liquid lens 18 is in a proportional relationship with the applied voltage. Furthermore, as shown in FIG. 10B, the response time from when the voltage is applied to the liquid lens 18 until the change of the focal position is completed becomes longer the farther (deeper) the focal position.

Therefore, the interval of the focal length will differ if the image of the measuring object 2 is picked up at a constant time interval, and an image suited to conversion to the three-dimensional coordinate is difficult to obtain. Thus, in the present embodiment, the image of the measuring object 2 is picked up at the times of t0, t1, t2, t3, and t4 corresponding to five positions of the focal lengths f0, f1, f2, f3, f4 while controlling the picking up timing such that the interval of the focal length becomes constant, as shown in FIG. 10B. The times t0, t1, t2, t3, and t4 are recorded in the image recording unit 33 as image taking time ST at T=1 (step S16).

The image taking operation is repeated until T≧i ("i" is a positive integer) (steps S17, S18). In this case, "i" is automatically set based on data obtained by the pre-scan. For example, "i"=3 if the guide light reflection surface of the measuring object 2 is positioned at the position (depth) of less than 10 mm from the light projecting unit 12. In this case, a range of voltage to apply to the liquid lens 18 is between 47 and 51 V. Furthermore, "i"=5 if the guide light reflection surface of the measuring object 2 is positioned at a position (depth) of greater than or equal to 10 mm from the light projecting unit 12. In this case, the range of voltage to apply to the liquid lens 18 is between 43 and 51 V.

When T≦i, a plurality of images n and image taking times are recorded in the image recording unit 33 in association to each other (step S19). Thereby, the image taking of the measuring object 2 is completed.

The three-dimensional image of higher accuracy can be synthesized the greater the number of images n. However, when taking a frame rate of a general CCD and hand instability at the time of image taking into consideration, the image taking is preferably completed within one second. Thus, a CMOS sensor enabling higher speed image taking is preferably used for the imaging sensor 17, and an algorithm enabling high accuracy image synthesis is preferably used.

Figure 11:
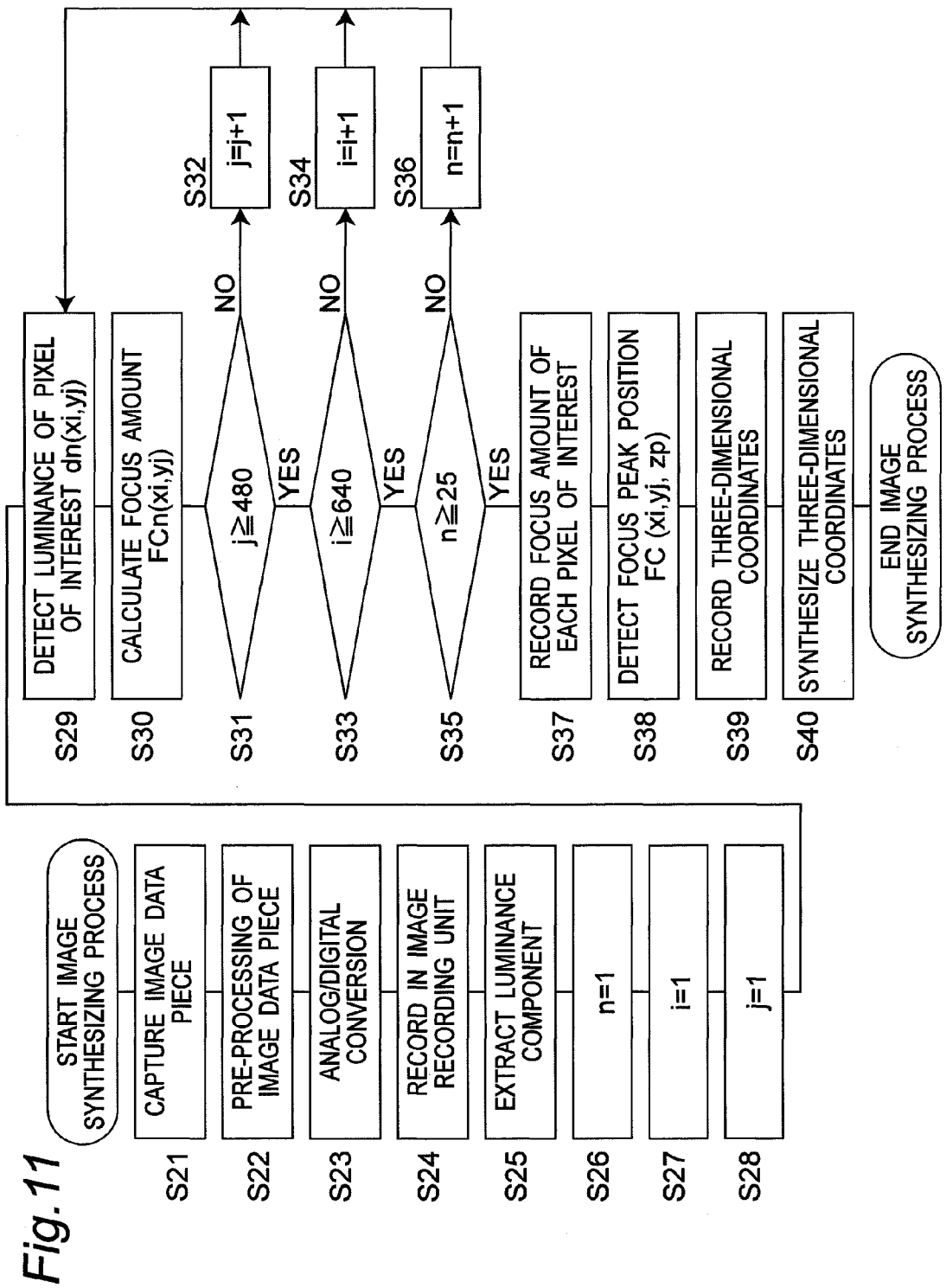
FIG. 11 is a flowchart showing a synthesizing process method of the three-dimensional image in the intra-oral measurement system according to the first embodiment of the present invention.

A synthesizing process method of the three-dimension image will now be described with reference to FIGS. 1, 5, and 11. FIG. 11 is a flowchart showing the synthesizing process method of the three-dimensional image in the intra-oral measurement system according to the first embodiment. In this case, description will be made assuming the CCD having 640×480 pixels is used for the imaging sensor 17, by way of example.

First, the two-dimensional image processing unit 34 captures the image data recorded in the image recording unit 33 (step S21).

Then, the two-dimensional image processing unit 34 performs pre-processing such as gray level correction and noise removal on the captured image data (step S22).

The two-dimensional image processing unit 34 converts the pre-processed signal from an analog signal to a digital signal (step S23).

The two-dimensional image processing unit 34 records the image data converted to the digital signal in the image recording unit 33 as a signal image (step S24).

The three-dimensional image converting unit 35 or 38 extracts luminance information (luminance value) to use for the calculation of the focal position from the signal image (step S25). In this case, the luminance information is given, by way of example, for information to use for the calculation of the focal position, but specific color information may be used instead of the luminance information. The information to use for the calculation of the focal position may be a maximum value, a minimum value, or the like of the luminance information or the color information.

Then, the three-dimensional image converting unit 35 or 38 selects a first image (n=1) recorded in the flow (step S19) of the image taking of the measuring object 2 (step S26).

The three-dimensional image converting unit 35 or 38 sets i, j for specifying x, y coordinates in the image to i=1, and j=1 (steps S27, S28).

The three-dimensional image converting unit 35 or 38 detects luminance of a pixel of interest dn(xi, yj) specified by n, i, j (step S29).

Then, the focus amount FCn(xi, yj) at the pixel of interest is calculated (step S30).

Figure 12A:
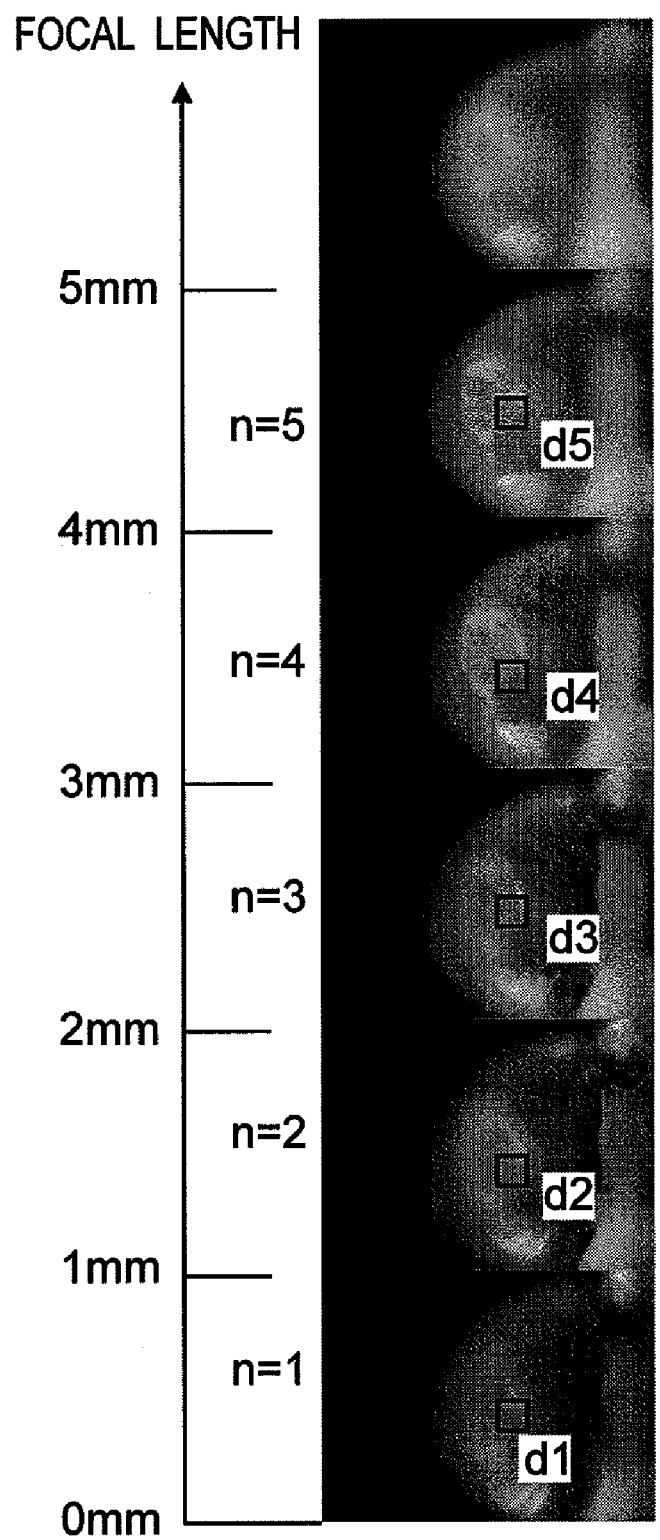
FIG. 12A is an explanatory view for calculation of a focus amount in the first embodiment of the present invention.
Figure 12B:
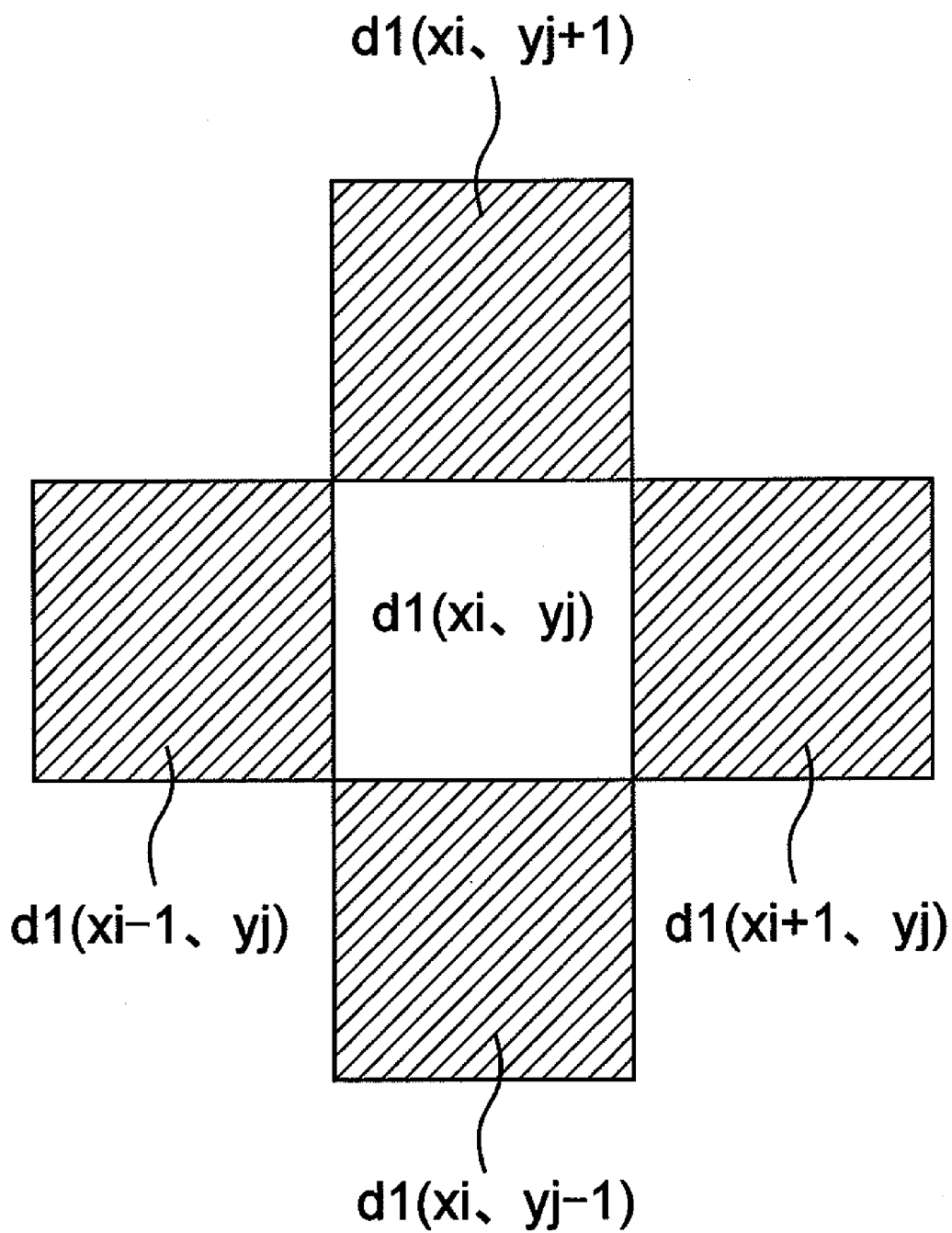
FIG. 12B is an explanatory view for the calculation of the focus amount in the first embodiment of the present invention.

FIGS. 12A and 12B are explanatory views for the calculation of the focus amount in the first embodiment. The focus amount FC1(xi, yj) of the pixel of interest d1(xi, yj) in the image of n=1 can be calculated from the following equation using four pixels d1(xi, yj+1), d1(xi−1, yj), d1(xi, yj−1), d1(xi−1, yj) adjacent to the pixel of interest.

$$FC1(xi,yj)=d1(xi,yj)-[d1(xi,yj+1)+d1(xi-1,yj)+d1(xi,yj-1)+d1(xi-1,yj)]/4 \qquad [\text{Equation 1}]$$

The calculation of the focus amount is performed until n≧25, i≧660, j≧480 by changing the values of n, i, j (steps S31 to S36).

The three-dimensional image converting unit 35 or 38 records the calculated focus amount of each pixel of interest in the three-dimensional image recording unit 36 (step S37).

The three-dimensional image converting unit 35 or 38 detects the focus peak position for every pixel from the focal length associated with each image and the calculated focus amount (step S38).

Figure 13:
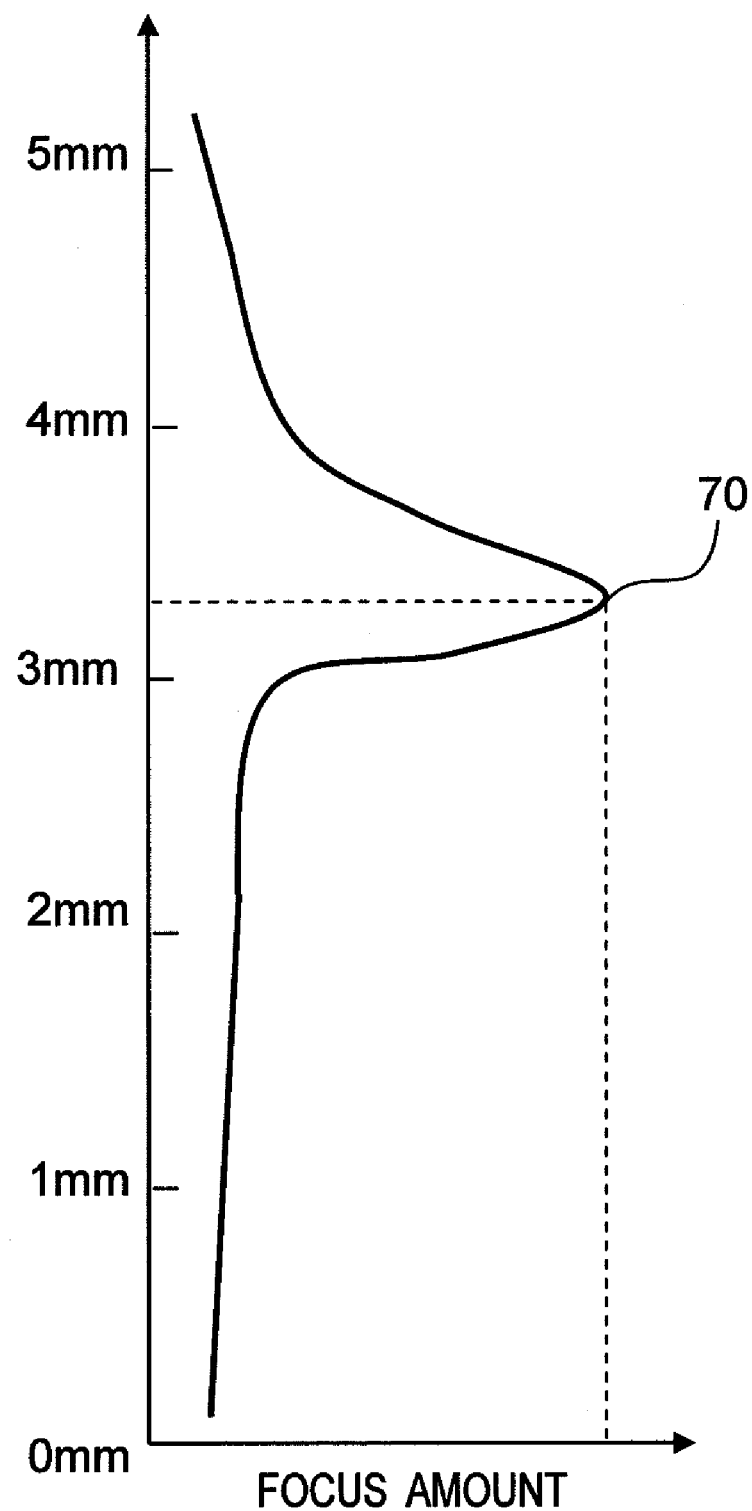
FIG. 13 is an explanatory view for detection of a focus peak position in the first embodiment of the present invention.

FIG. 13 is an explanatory view for the detection of the focus peak position in the first embodiment, and is a diagram in which the focal length associated with each image and the calculated focus amount are plotted for one pixel of interest. A position 70 where the focus amount becomes a peak, as shown in FIG. 13, exists for every pixel of interest. The three-dimensional image converting unit 35 or 38 detects the peak position 70 and records the focal length corresponding to the peak position 70 in the three-dimensional image recording unit 36 as the z coordinate of the relevant pixel of interest. In other words, the three-dimensional coordinate is recorded in the three-dimensional image recording unit 36 (step S39).

Figure 14:
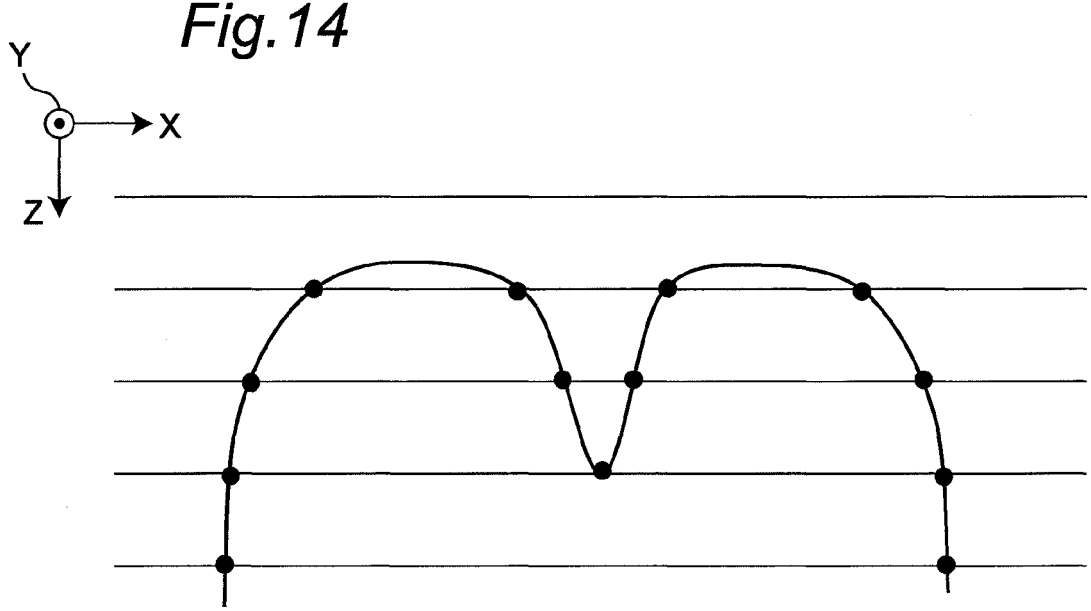
FIG. 14 is an explanatory view showing an image of synthesizing coordinates.

Then, the three-dimensional coordinates recorded in the three-dimensional image recording unit 36 are synthesized (step S40). FIG. 14 is an explanatory view showing an image of synthesizing the coordinates.

The three-dimensional image as shown in FIG. 8 is obtained by performing the flow of steps S21 to S40 above.

According to the intra-oral measurement system equipped with the oral scanner 1 of the first embodiment, plurality of images with different focal positions can be obtained by imaging with the imaging sensor 17 while changing the focal position with the liquid lens 18. The plurality of images obtained in such a manner can be transformed to a three-dimensional coordinate using the DFD method. Therefore, according to the intra-oral measurement system of the first embodiment, the inside of the oral cavity can be measured at high accuracy without increasing the size of the device since the triangulation method is not used as in the related art. In the intra-oral measurement system of the present invention, a great number of images having different focal positions is to be imaged in order to measure the inside of the oral cavity at high accuracy.

Figure 15:
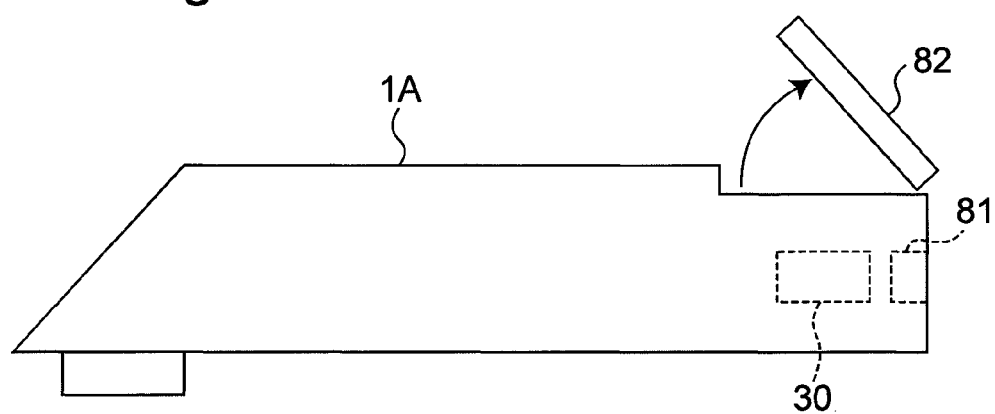
FIG. 15 is an explanatory view showing a schematic configuration of an oral scanner incorporating an image processing unit.

The present invention is not limited to the first embodiment, and can be implemented in various other modes. For example, the intra-oral measurement system in which the image processing unit 30 is housed in the external device 40 has been described in the first embodiment, but the present invention is not limited thereto. The image processing unit 30 may be built in the oral scanner 1A, as shown in FIG. 15. In this case, as shown in FIG. 15, a data capturing mechanism 81 for exteriorly capturing the data of the three-dimensional coordinate of the measuring object 2 measured by the oral scanner 1A is arranged in the oral scanner 1A. The data capturing mechanism 81 is, for example, a connector of a cable, a transmission/reception unit of wireless communication, or a slot of an SD memory card. As shown in FIG. 15, if a small display unit 82, which angle can be varied, is arranged in the oral scanner 1A, necessity to connect the oral scanner 1A to the external device 40 including the display unit 41 can be eliminated, and convenience can be further enhanced.

The prism 15 is arranged in the first embodiment, but the prism 15 does not necessarily need to be arranged.

Second Embodiment

Figure 16:
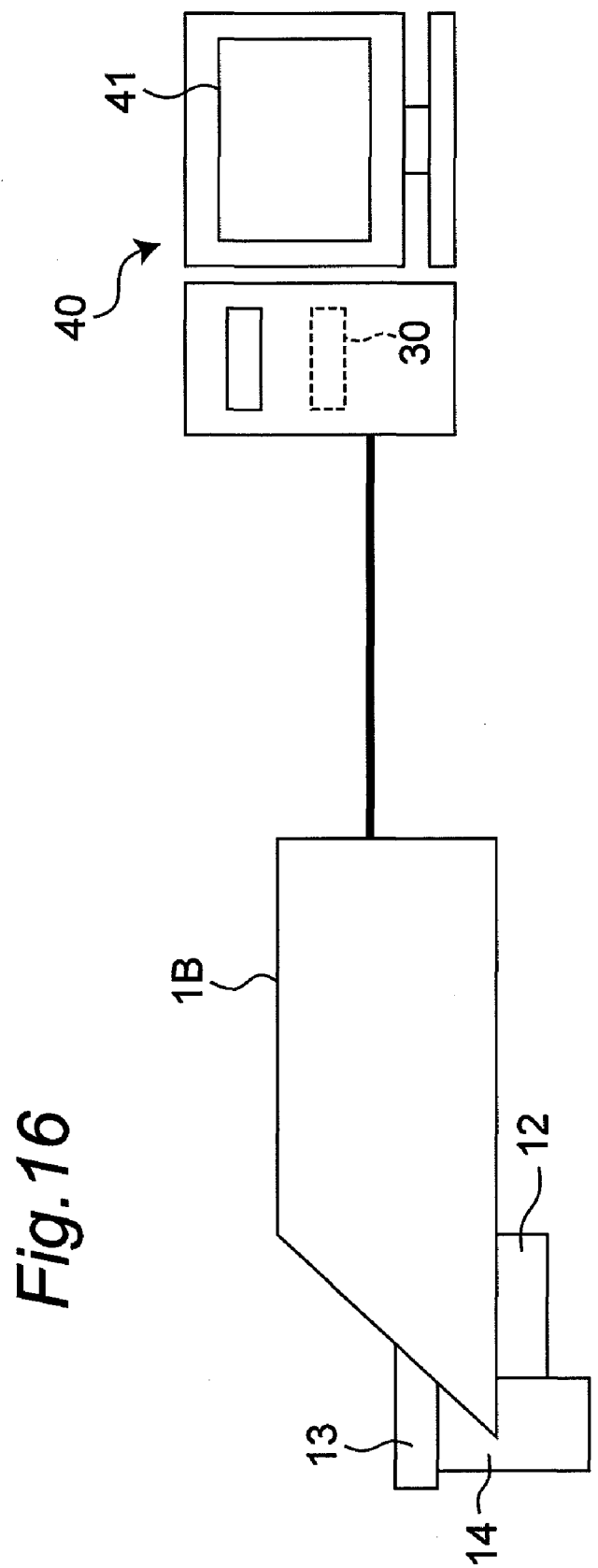
FIG. 16 is an explanatory view showing a schematic configuration of an intra-oral measurement system including an oral scanner according to a second embodiment of the present invention.
Figure 17:
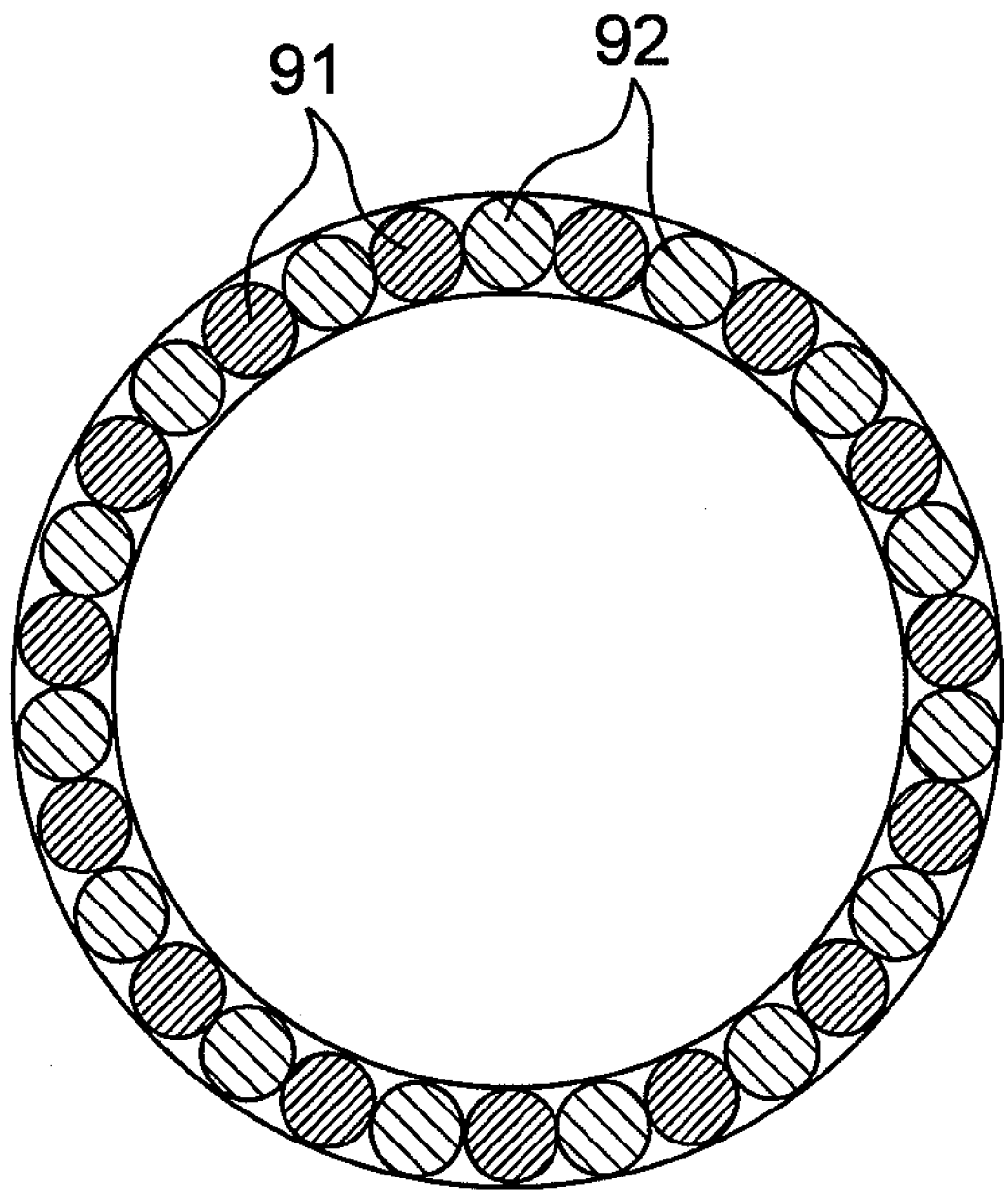
FIG. 17 is a schematic view of a light projecting unit of the oral scanner shown in FIG. 16 seen from downside.

FIG. 16 is an explanatory view showing a schematic configuration of an intra-oral measurement system including an oral scanner 1B according to a second embodiment of the present invention. FIG. 17 is a schematic view of the light projecting unit of the oral scanner shown in FIG. 16 seen from downside. The intra-oral measurement system according to the second embodiment differs from the intra-oral measurement system according to the first embodiment in that a light projecting unit 12A including two types of light sources having different wavelengths is arranged in place of the light projecting unit 12, and in that a wavelength control unit (not shown) connected to the image taking control unit 31 is arranged in the image processing unit 30.

A shape within the oral cavity is different for every patient. The surface reflectivity of light of each tissue differs due to difference in a state of tooth decay, enamel and dentine configuring the tooth, and a composition of the gingivae. Thus, a clear image cannot be imaged with the light source of one type of wavelength, and an accurate shape of the measuring object 2 (tooth and gingivae) may not be measured. To improve such an issue, powder of titanium oxide and the like is sprayed into the oral cavity to even the reflectivity inside the oral cavity in the above-mentioned Selleck system of the related art.

However, evenly spraying the powder into the oral cavity is difficult, and even if possible, a state in which the powder is evenly sprayed into the oral cavity is difficult to maintain due to an influence of saliva and the like. The sprayed powder needs to be washed away after the inside of the oral cavity is measured, which is troublesome.

TABLE 1

| | Light projection wavelength | |
|---|---|---|
| | 500~565 nm | 625~740 nm |
| Enamel | ○ | X |
| Dentine | Δ | ○ |
| Gingivae | X | ○ |

Table 1 shows whether or not images of enamel, dentine, and gingivae serving as the imaged measuring object 2 are clear (in a good condition) for when the wavelength of the light emitted from the light projecting unit is between 500 nm and 565 nm and for when between 625 nm and 740 nm. In table 1, "○" (circle) is given for when clear, "Δ" (triangle) for when slightly unclear, and "X" (cross mark) for when unclear. As shown in table 1, the enamel was clear when irradiated with light having the wavelength of between 500 nm and 565 nm, but the dentine was slightly unclear and the gingivae was unclear. When irradiated with light having the wavelength of between 625 nm and 740, the enamel was unclear, but the dentine and the gingivae were clear. In other words, the enamel has high surface reflectivity with respect to the light having the wavelength of between 500 nm and 565 nm, and the dentine and the gingivae have high surface reflectivity with respect to the light having the wavelength of between 625 nm and 740 nm.

Therefore, in the second embodiment, a first light source 91 for projecting the light having the wavelength of between 500 nm and 565 nm, and a second light source 92 for projecting the light having the wavelength of between 625 nm and 740 nm configure the light projecting unit 12A. Thus, a clear image can be obtained for all of enamel, dentine, and gingivae.

When imaging the enamel, the dentine, and the gingivae using the light projecting unit 12 configured as above, the image taking operation of steps S11 to S19 (FIG. 9) are repeated twice for a process A and a process B. The process A is a process of steps S11 to S19 (FIG. 9) in which the light is emitted from the first light source 91, and the process B is a process of steps S11 to S19 (FIG. 9) in which the light is emitted from the second light source 92.

In image synthesizing, for example, the tooth portion and the gingivae portion are separated, so that the image synthesizing process is performed using the image imaged by irradiating the tooth portion with the light from the first light source 91, and the image synthesizing process is performed using the image imaged by irradiating the gingivae portion with the light from the second light source 92.

The light projecting unit 12A merely needs to be able to emit light having a plurality of (two or more) different wavelengths. The light projecting unit 12A may be configured by a plurality of LEDs having different wavelengths. The light projecting unit 12A may be configured to branch the light of the laser light source at a distant position with a plurality of fibers, and irradiate the light having different wavelengths through the fibers. A filter for displacing the wavelength may be placed on the light projecting unit 12 of the first embodiment to irradiate the light having a plurality of different wavelengths.

Third Embodiment

Figure 18:
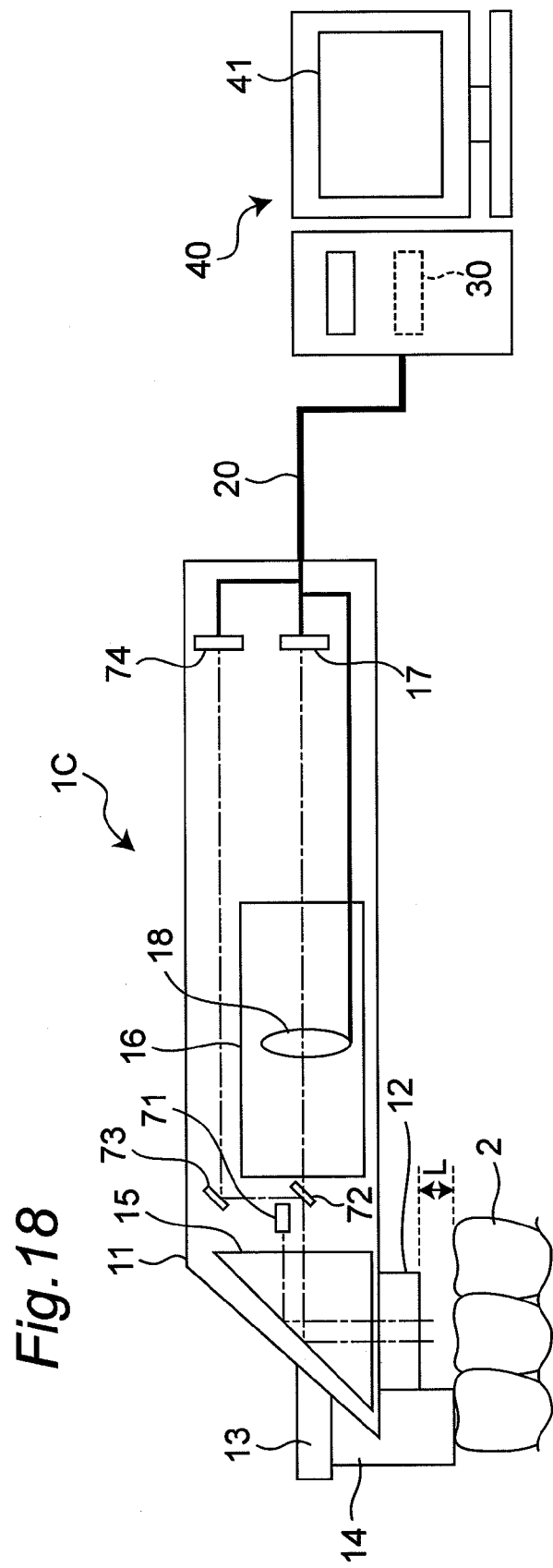
FIG. 18 is an explanatory view showing a schematic configuration of an oral scanner according to a third embodiment of the present invention.

FIG. 18 is an explanatory view showing a schematic configuration of an intra-oral measurement system including an oral scanner 1C according to a third embodiment of the present invention. The intra-oral measurement system according to the third embodiment differs from the intra-oral measurement system according to the first embodiment in that a pre-scan light source 71 serving as a pre-scan light projecting device, mirrors 72, 73, and a line sensor 74 are arranged in place of the spot light source 19.

As described above, since the positioning of the oral scanner 1C is performed by the dentist, the pre-scan surface normally inclines with respect to the irradiation direction of the guide light. In the first embodiment, an inclination angle of the pre-scan surface with respect to the irradiation direction of the guide light is examined by examining the circularity and the like of the guide light. Specifically, the configuration is as described below.

Figure 19:
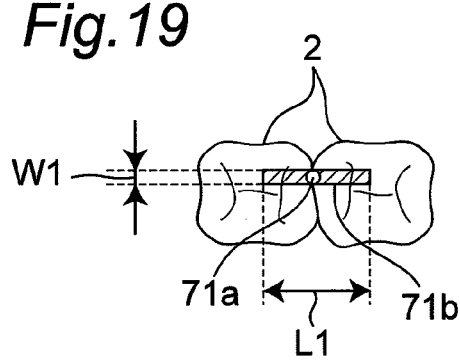
FIG. 19 is a plan view showing guide light emitted by a line light source.

The pre-scan light source 71 has functions of both the spot light source and the line light source. In other words, as shown in FIG. 19, the pre-scan light source 71 is configured to irradiate a guide light 71a towards the prism 15 so as to focus at a distant position set in advance from the distal end of the light projecting unit 12, and to irradiate a linear light 71b passing through the relevant position towards the prism 15. The guide light 71a is reflected by the measuring object 2 and enters the prism 15, and then refracted by the prism 15, passed through the liquid lens 18, and received by the imaging sensor 17. The linear light 71b is reflected by the measuring object 2 and enters the prism 15, refracted by the prism 15 and the mirrors 72, 73, and received by the line sensor 74. The image received by the imaging sensor 17 and the information of the light 71b received by the line sensor 74 are sent to the image processing unit 30 through the transfer cable 20.

When the linear light 71b is projected onto the measuring object 2 with the pre-scan surface inclined with respect to the irradiation direction of the guide light 71a, the linear light 71b will not be a straight light but a curved line. The pre-scan data recording unit 39 stores in advance the relationship between the shape of the light 71b projected on the measuring object 2 and the inclination angle of the pre-scan surface with respect to the irradiation direction of the guide light 71a. The image processing unit 30 examines the depth of the reflection point of the guide light 71a based on the image blur amount of the measuring object 2 received by the imaging sensor 17, and examines the inclination angle of the pre-scan surface with respect to the irradiation direction of the guide light 71a based on the shape of the light 71b projected on the measuring object 2. Thus, the measurement accuracy of the pre-scan can be enhanced.

A width W1 of the linear light 71b is preferably as small as possible (e.g., smaller than or equal to 1.0 mm), similar to a spot diameter of the guide light 71a. A change in shape is difficult to recognize if a length L1 of the linear light 71b is short, and thus the length is preferably set to be greater than or equal to 20 mm.

In the third embodiment, a transmissive liquid crystal may be arranged between the pre-scan light source 71 and the prism 15 to switch between the spot light source and the line light source.

In the third embodiment, functions of both the spot light source and the line light source are given to the pre-scan light source 71 to examine the reflection point of the guide light 71a, but the present invention is not limited thereto. For example, the depth of the reflection surface of the guide light 71a can be examined even when the pre-scan light source 71 has the function of the line light source for irradiating light of triangular prism shape instead of the linear shape (band shape).

Fourth Embodiment

Figure 20:
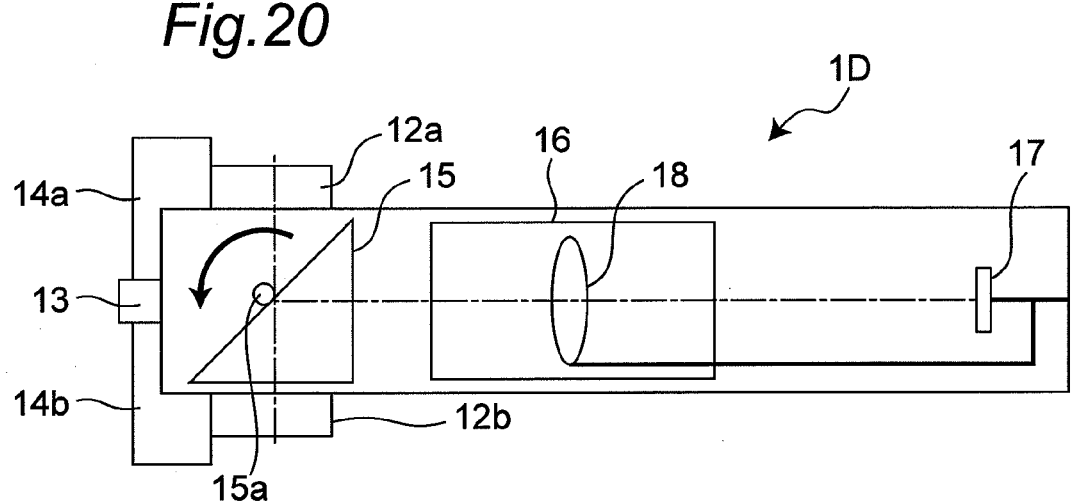
FIG. 20 is an explanatory view showing a schematic configuration of an intra-oral measurement system including an oral scanner according to a fourth embodiment of the present invention.
Figure 21:
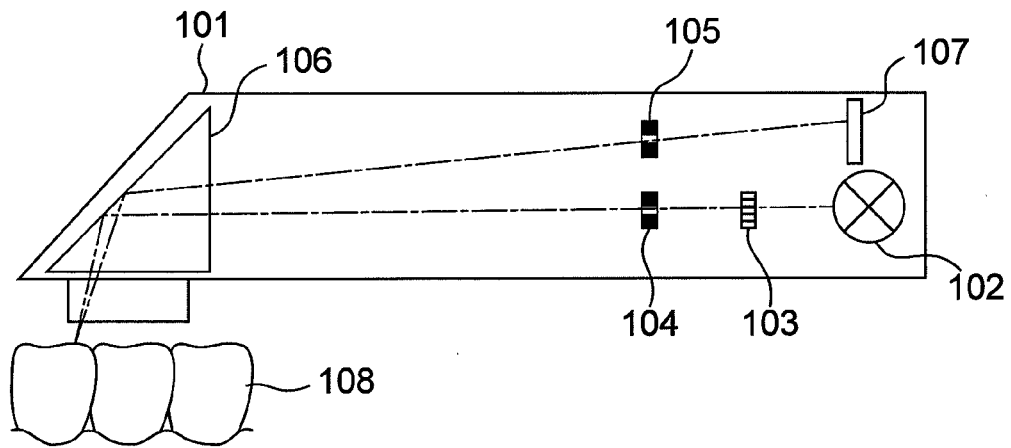
FIG. 21 is an explanatory view showing a configuration of an optical three-dimensional camera according to a conventional example.

FIG. 20 is an explanatory view showing a schematic configuration of an intra-oral measurement system including an oral scanner 1D according to a fourth embodiment of the present invention. The intra-oral measurement system according to the fourth embodiment differs from the intra-oral measurement system according to the first embodiment in that light projecting units 12a, 12b and rubbers 14a, 14b are both arranged in an up and down direction of the figure.

In other words, the oral scanner 1D of the fourth embodiment has a configuration of being able to measure shapes of upper and lower teeth to take into consideration occlusion of the teeth. As a specific configuration, the prism 15 is rotatable with a shaft 15a as a rotating shaft, so that the measurement of the lower tooth using the light projecting unit 12b on the lower tooth side can be performed in the state shown in FIG. 20 and the measurement of the upper tooth using the light projecting unit 12a on the upper tooth side can be performed in a state the prism 15 is rotated.

Since the rubber 14a, 14b are arranged at both the up and down directions of the oral scanner 1, the oral scanner 1 can be fixed at a position of occlusion of the teeth by biting the rubbers 14a, 14b with the upper tooth and the lower tooth. Thus, the shape of the upper tooth and the lower tooth in the occlusion state of the teeth can be measured.

By properly combining arbitrary embodiments of the aforementioned various embodiments, the effects owned by each of them can be made effectual.

According to the present invention, the inside of the oral cavity can be measured at high accuracy without increasing the size of the device, and thus the present invention is particularly useful in a system of designing and fabricating the dental prosthesis.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

The entire disclosure of Japanese Patent Application No. 2009-016321 filed on Jan. 28, 2009, including specification, claims, drawings, and summary are incorporated herein by reference in its entirety.

The invention claimed is:

1. An intra-oral measurement device comprising:
a light projecting unit for irradiating a measuring object including at least a tooth within an oral cavity with light;
a lens system unit for collecting light reflected by the measuring object;
a focal position varying mechanism for changing a focal position of the light collected by the lens system unit;
an imaging unit for imaging light passed through the lens system unit;
a pre-scan light projecting device for emitting guide light focused at a position distant from the light projecting unit by a distance set in advance; and
an image processing unit, which without image the light passed through the lens system unit with the imaging unit when a circularity of the guide light emitted from the pre-scan light projecting device and projected onto the measuring object is lower than a threshold value set in advance, and images the light passed through the lens system unit with the imaging unit when the circularity of the guide light is higher than the threshold value set in advance.

2. The intra-oral measurement device according to claim 1, wherein a liquid lens is used for the focal position varying mechanism.

3. The intra-oral measurement device according to claim 2, further comprising a gap retaining member for holding a gap between the tooth and the light projecting unit constant.

4. The intra-oral measurement device according to claim 1, wherein the pre-scan light projecting device emits linear light passing through the position distant from the light projecting unit by the distance set in advance.

5. The intra-oral measurement device according to claim 4, further comprising a gap retaining member for holding a gap between the tooth and the light projecting unit constant.

6. The intra-oral measurement device according to claim 1, further comprising a three-dimensional image converting unit for calculating three-dimensional coordinates of the measuring object using a plurality of images, having different focal positions, imaged by the imaging unit.

7. The intra-oral measurement device according to claim 6, wherein the three-dimensional image converting unit calculates the three-dimensional coordinates of the measuring object using the images having different focal positions associated with a response speed of the focal position varying mechanism.

8. The intra-oral measurement device according to claim 7, further comprising a gap retaining member for holding a gap between the tooth and the light projecting unit constant.

9. The intra-oral measurement device according to claim 6, further comprising a gap retaining member for holding a gap between the tooth and the light projecting unit constant.

10. The intra-oral measurement device according to claim 1, wherein the light projecting unit irradiates an inside of the oral cavity with light having a plurality of different wavelengths.

11. The intra-oral measurement device according to claim 10, further comprising a gap retaining member for holding a gap between the tooth and the light projecting unit constant.

12. The intra-oral measurement device according to claim 10, wherein the light having different wavelengths includes light having a wavelength of between 500 and 565 nm, and light having a wavelength of between 625 and 740 nm.

13. The intra-oral measurement device according to claim 12, further comprising a gap retaining member for holding a gap between the tooth and the light projecting unit constant.

14. The intra-oral measurement device according to claim 1, further comprising a gap retaining member for holding a gap between the tooth and the light projecting unit constant.

15. The intra-oral measurement device according to claim 14, wherein the gap retaining member has a two-layered structure in which a distal end portion, which is a side that comes in contact with the tooth, is soft and a main body portion, which is a side fixed to the device, is harder than the distal end portion.

16. An intra-oral measurement device comprising:
a light projecting unit for irradiating a measuring object including at least a tooth within an oral cavity with light;
a lens system unit for collecting light reflected by the measuring object;
a focal position varying mechanism for changing a focal position of the light collected by the lens system unit;
an imaging unit for imaging light passed through the lens system unit;
a pre-scan light projecting device for emitting guide light focused at a position distant from the light projecting unit by a distance set in advance; and
an image processing unit, which without image the light passed through the lens system unit with the imaging unit when an amount of shift between a light quantity distribution of the guide light emitted from the pre-scan light projecting device and projected onto the measuring object and an ideal light quantity distribution of the guide light is lower than a threshold value set in advance, and images the light passed through the lens system unit with the imaging unit when the amount of shift is higher than the threshold value set in advance.

17. The intra-oral measurement device according to claim 16, further comprising a gap retaining member for holding a gap between the tooth and the light projecting unit constant.

18. An intra-oral measurement system comprising:
a light projecting unit for irradiating a measuring object including at least a tooth within an oral cavity with light;
a lens system unit for collecting light reflected by the measuring object;
a focal position varying mechanism for changing a focal position of the light collected by the lens system unit;
an imaging unit for imaging light passed through the lens system unit;
a three-dimensional image converting unit for calculating three-dimensional coordinates of the measuring object using a plurality of images, having different focal positions, imaged by the imaging unit;
a pre-scan light projecting device for emitting guide light focused at a position distant from the light projecting unit by a distance set in advance; and
an image processing unit, which without image the light passed through the lens system unit with the imaging unit when a circularity of the guide light emitted from the pre-scan light projecting device and projected onto the measuring object is lower than a threshold value set in advance, and images the light passed through the lens system unit with the imaging unit when the circularity of the guide light is higher than the threshold value set in advance.

19. An intra-oral measurement system comprising:
a light projecting unit for irradiating a measuring object including at least a tooth within an oral cavity with light;
a lens system unit for collecting light reflected by the measuring object;
a focal position varying mechanism for changing a focal position of the light collected by the lens system unit;
an imaging unit for imaging light passed through the lens system unit;
a three-dimensional image converting unit for calculating three-dimensional coordinates of the measuring object using a plurality of images, having different focal positions, imaged by the imaging unit;
a pre-scan light projecting device for emitting guide light focused at a position distant from the light projecting unit by a distance set in advance; and
an image processing unit, which without image the light passed through the lens system unit with the imaging unit when an amount of shift between a light quantity distribution of the guide light emitted from the pre-scan light projecting device and projected onto the measuring object and an ideal light quantity distribution of the guide light is lower than a threshold value set in advance, and images the light passed through the lens system unit with the imaging unit when the amount of shift is higher than the threshold value set in advance.

* * * * *